(12) United States Patent
Truman

(10) Patent No.: US 8,652,183 B1
(45) Date of Patent: Feb. 18, 2014

(54) MULTI-ANGLE ORTHOPEDIC EXPANSION HEAD FASTENER

(76) Inventor: Mari S Truman, Warsaw, IN (US)

(*) Notice: Subject to any disclaimer, the term of this patent is extended or adjusted under 35 U.S.C. 154(b) by 311 days.

(21) Appl. No.: 12/831,753

(22) Filed: Jul. 7, 2010

Related U.S. Application Data

(60) Provisional application No. 61/223,517, filed on Jul. 7, 2009.

(51) Int. Cl.
*A61B 17/86* (2006.01)
*A61B 17/88* (2006.01)

(52) U.S. Cl.
USPC ................................. 606/305; 606/281

(58) Field of Classification Search
USPC ............... 606/281, 286–296, 305–308, 315, 606/325–327; 411/354
See application file for complete search history.

(56) References Cited

U.S. PATENT DOCUMENTS

| | | | |
|---|---|---|---|
| 3,596,656 A | 8/1971 | Kaute | |
| 3,741,205 A | 6/1973 | Markolf | |
| 3,906,550 A | 9/1975 | Rostoker et al. | |
| 4,146,022 A | 3/1979 | Johnson et al. | |
| 4,338,926 A | 7/1982 | Kummer et al. | |
| 4,969,888 A | 11/1990 | Scholten et al. | |
| 5,108,399 A | 4/1992 | Eitenmuller et al. | |
| 5,108,404 A | 4/1992 | Scholten et al. | |
| 5,198,308 A | 3/1993 | Shetty et al. | |
| 5,259,398 A | 11/1993 | Vrespa | |
| 5,275,601 A | 1/1994 | Gogolewski et al. | |
| 5,487,741 A | 1/1996 | Maruyama et al. | |
| 5,534,027 A | 7/1996 | Hodorek | |
| 5,605,713 A | 2/1997 | Boltong | |
| 5,607,426 A | 3/1997 | Ralph et al. | |
| 5,611,800 A * | 3/1997 | Davis et al. | 606/250 |
| 5,658,310 A | 8/1997 | Berger | |
| 5,683,460 A | 11/1997 | Persoons | |
| 5,709,686 A | 1/1998 | Talos et al. | |
| 5,735,853 A | 4/1998 | Olerud | |
| 5,797,912 A | 8/1998 | Runciman et al. | |
| 5,851,207 A * | 12/1998 | Cesarone | 606/86 B |
| 5,863,201 A | 1/1999 | Lazzara et al. | |
| 5,954,722 A | 9/1999 | Bono | |
| 5,972,015 A | 10/1999 | Schribner et al. | |
| 6,206,881 B1 | 3/2001 | Frigg et al. | |
| 6,322,562 B1 | 11/2001 | Wolter | |
| 6,368,326 B1 | 4/2002 | Daken et al. | |
| 6,565,960 B2 | 5/2003 | Koob et al. | |
| 6,610,079 B1 | 8/2003 | Li et al. | |
| 6,878,758 B2 | 4/2005 | Martin et al. | |
| 6,908,473 B2 | 6/2005 | Skiba et al. | |

(Continued)

*Primary Examiner* — Todd Manahan
*Assistant Examiner* — Eric S Gibson
(74) *Attorney, Agent, or Firm* — Sheldon H. Parker, Esq.

(57) ABSTRACT

The disclosed fasteners have a substantially cylindrical expansion head to secure the fastener in a support structure. The expansion fastener has a removable locking ring, a head, and a shaft extending from the distal end of the head. The exterior of the head has at least one slot extending from the edge toward the distal end. The slots can extend partially or fully to the base of the head. In one embodiment the locking ring has at least one tab that extends beyond the periphery and a tool receiving area. In one embodiment a channel having wall periphery reduction area receives a locking ring with tabs which, when rotated to contact the reduction areas expand the head. In another embodiment the locking ring has a threaded periphery that interacts with a reduced diameter threaded periphery within the head to expand the exterior of the head.

15 Claims, 29 Drawing Sheets

(56) References Cited

U.S. PATENT DOCUMENTS

| | | | |
|---|---|---|---|
| 6,953,594 | B2 | 10/2005 | Lee et al. |
| 6,955,677 | B2 | 10/2005 | Dahners |
| 6,974,461 | B1 | 12/2005 | Wolter |
| 6,979,341 | B2 | 12/2005 | Scribner et al. |
| 6,997,940 | B2 | 2/2006 | Bonutti |
| 7,153,306 | B2 | 12/2006 | Ralph et al. |
| 7,691,133 | B2 * | 4/2010 | Partin et al. .......... 606/289 |
| 7,736,380 | B2 * | 6/2010 | Johnston et al. ....... 606/280 |
| 2004/0068261 | A1 * | 4/2004 | Fourcault et al. ....... 606/67 |
| 2005/0154392 | A1 * | 7/2005 | Medoff et al. .......... 606/69 |
| 2005/0251137 | A1 * | 11/2005 | Ball .................... 606/61 |
| 2006/0122604 | A1 * | 6/2006 | Gorhan et al. ......... 606/69 |
| 2006/0167456 | A1 * | 7/2006 | Johnston et al. ....... 606/69 |
| 2009/0012571 | A1 * | 1/2009 | Perrow et al. ......... 606/280 |
| 2009/0192553 | A1 * | 7/2009 | Maguire et al. ....... 606/305 |
| 2009/0216282 | A1 * | 8/2009 | Blake et al. .......... 606/286 |
| 2010/0211116 | A1 * | 8/2010 | Suh et al. ............ 606/305 |
| 2012/0179207 | A1 * | 7/2012 | Mekhail et al. ....... 606/281 |

* cited by examiner

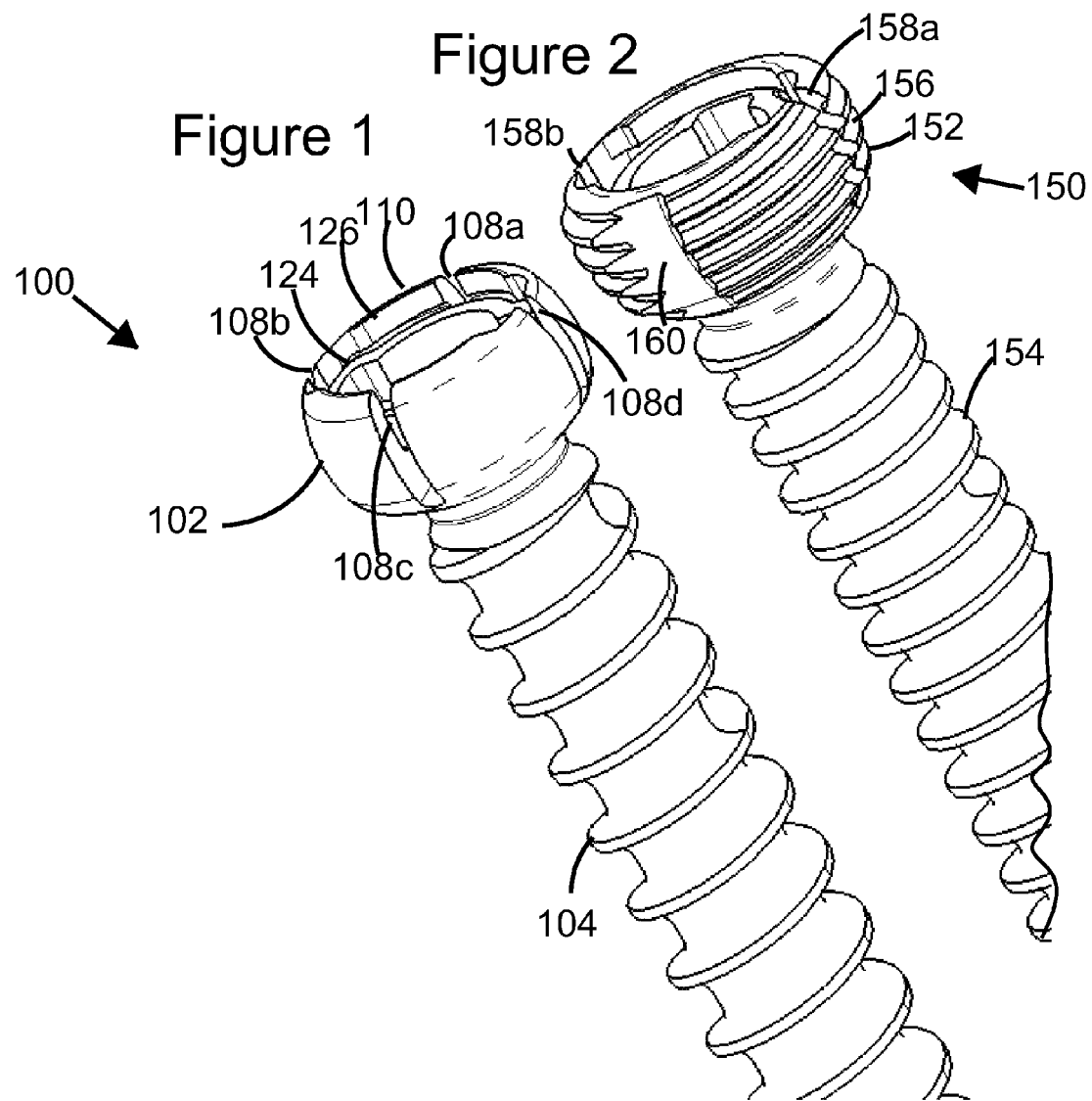

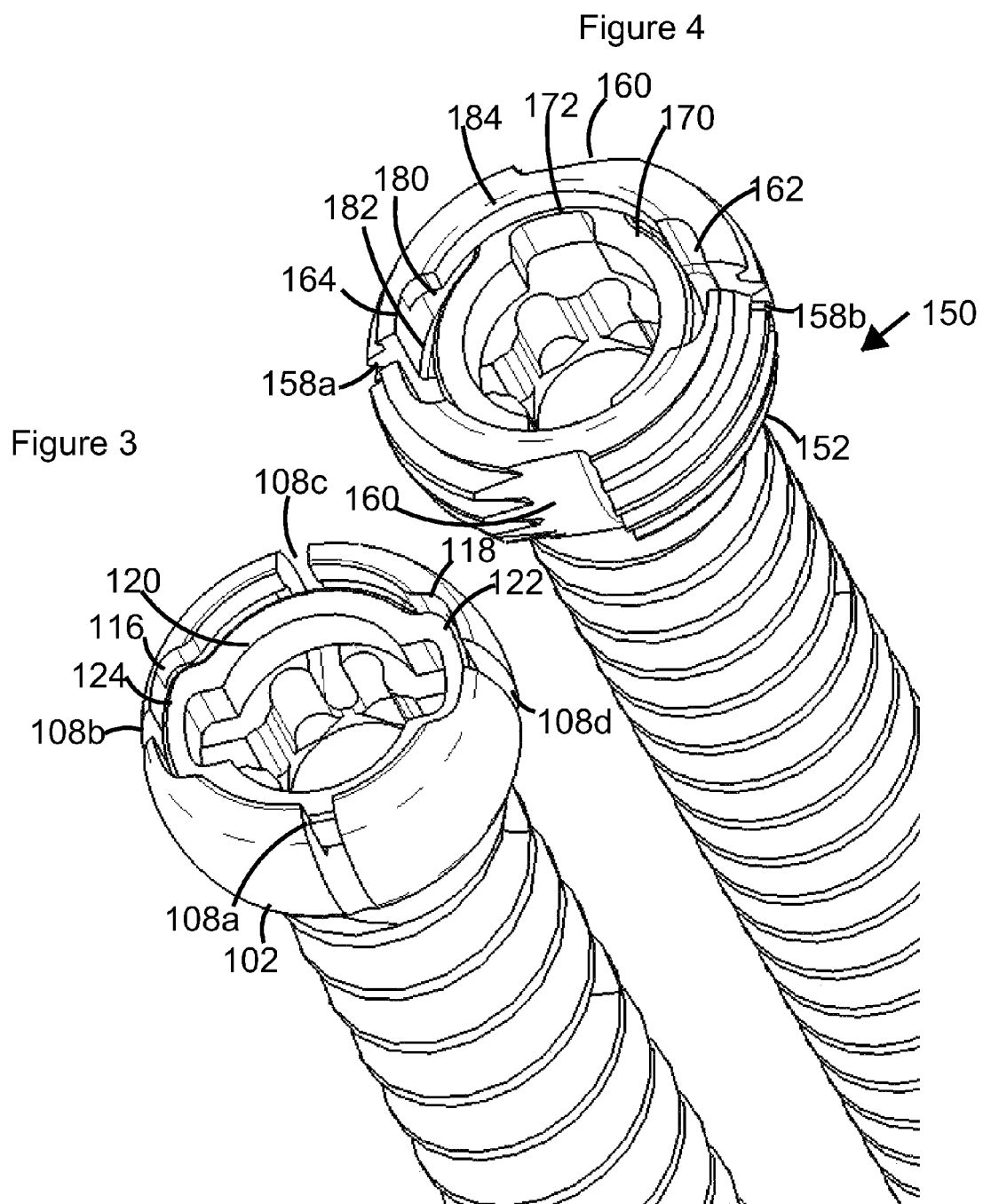

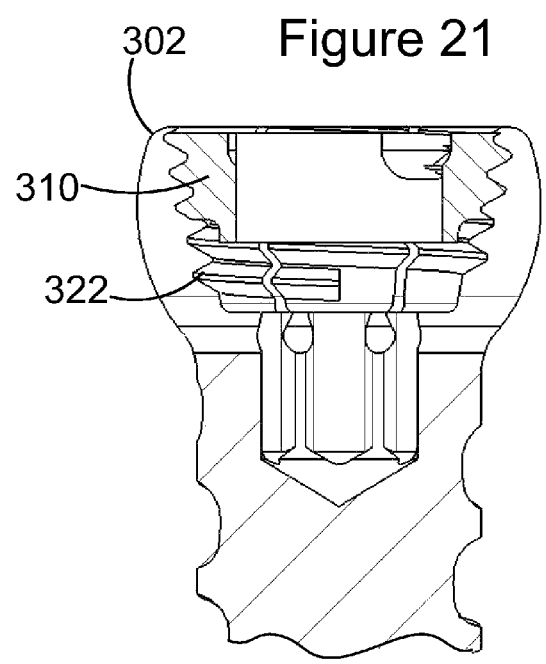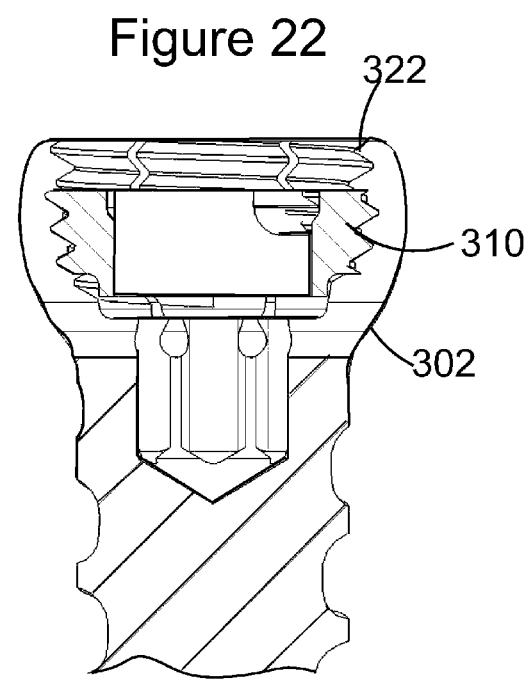

Figure 31
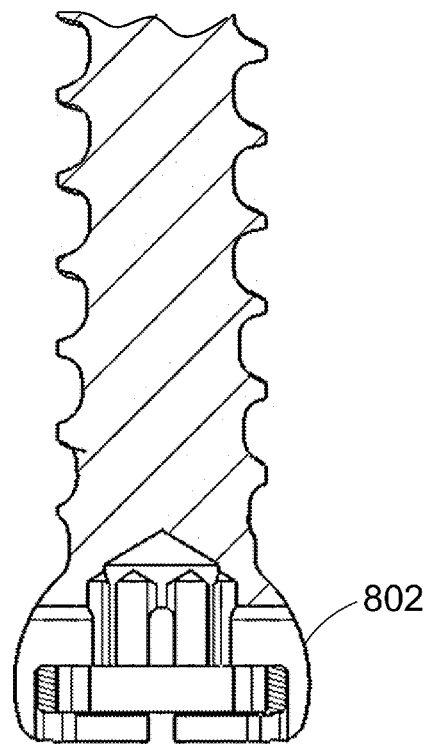
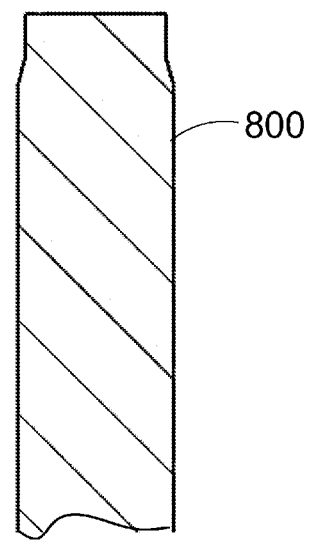

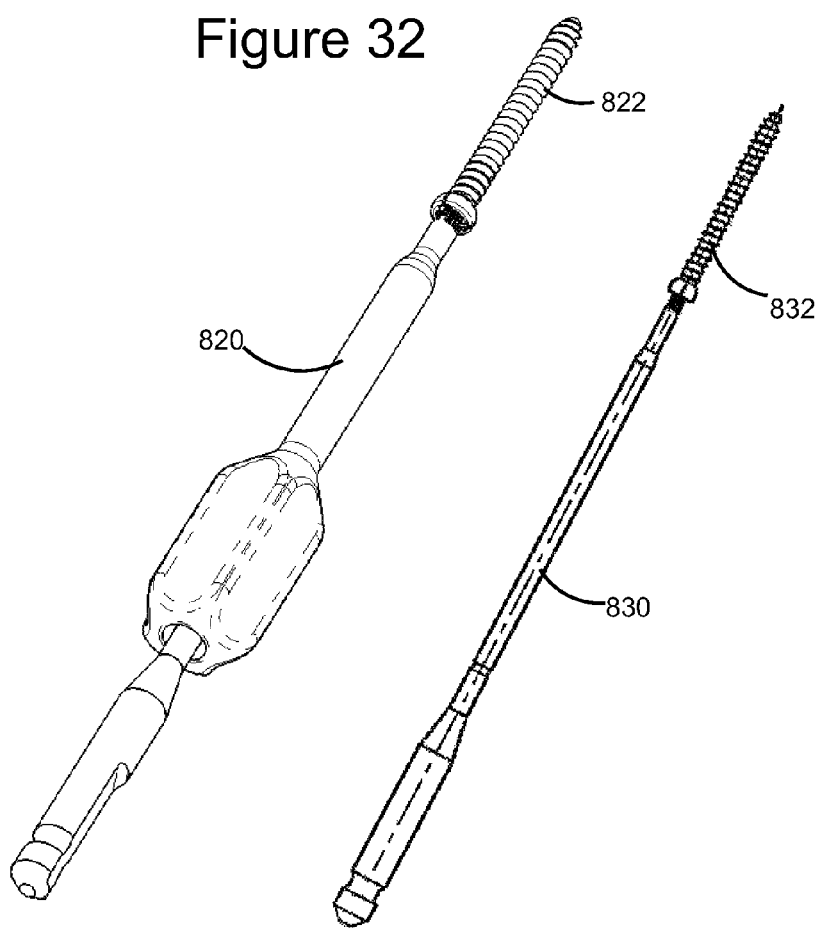

MULTI-ANGLE ORTHOPEDIC EXPANSION HEAD FASTENER

CROSS REFERENCE TO RELATED APPLICATIONS

This application is a non-provisional of U.S. 61/223,517 filed Jul. 7, 2009 which is incorporated by reference as though recited in full.

BACKGROUND

1. Field of the Invention

The invention relates general to biomedical fasteners and in particular to fasteners having an expandable head for the internal stabilization of a fractured bone and/or tissue.

2. Brief Description of the Prior Art

A variety of techniques exist in the field of osteosynthesis for treating bone fractures. Many known techniques utilize bone screws and bone fixation plates wherein the bone screws are connected to the ends of the bone and the connection carrier bridges the fracture. The connection carrier can in particular be a bone plate, a marrowbone nail or a fixator. With this it is desirable, whilst adapting to the nature of the bone part to be connected, for the optical alignment onto the fragments or for compensating target errors, to be able to incorporate fasteners, such as bone screws, at different angles into the connection carrier.

Many bone screws have heads with a roughly hemispherical-shaped seat surface of which one seat surface in passage holes is allocated to a bone plate. If for example with a tibia fracture the two bone pieces must be connected to one another, the metallic bone plate is applied onto the set-up bone pieces. Thereafter the screws are rotated into the bones such that the seat surfaces of the screw heads and of the plate holes come to bear on one another and the plate is pressed against the bone. From this there results a connection of bone parts, bone plate and bone screws.

It however has been shown that a loosening of the connection of bone screws and bone plates can take place. One cause lays in the insufficient stability of the angle connections of bone screw and bone plate which are secured by friction forces between the screw head and the plate hole. To resolve this problem an angular stable connection of the bone screw and bone plate must be made.

Simple mid-shaft fractures of bones are readily treated by bringing the fracture surfaces together and holding them in the desired orientation with respect to one another through the use of splints, casts and the like. Bones in general have dense outer, strong cortical portions and interior, non-cortical portions that may include cancellous bone. At the ends of bones this strong cortical region is typically thinner and the underlying cancellous bone tends to be a fluid filled porous medium which provides more "motion" and dissipates greater energy with transmission.

Comminuted fractures and fractures involving the breakage of a bone into numerous bone fragments are more difficult to deal with since one must attempt to reposition each bone fragment in an orientation relative to each other bone fragment so that the fragments may knit together properly. For this purpose, physicians have often used metal plates that attach to the outer cortical surfaces of the bones and which utilize bone screws to hold the bone fragments in position.

Another method involves the use of cerclage procedures in which a wire is, in effect, wrapped about a broken bone (or the bone and bone plate) to hold the fragments in place, the cerclage wire occasionally penetrating through the bone. Reference is made to Johnson et al., U.S. Pat. No. 4,146,022. Yet another common method is fixation of fragments with splints which are internal to the bone's medullary cavity. These are classified as intramedullary rods or interamedullary fixation devices. These devices may be metallic or polymeric, and typically involve a means to affix the ends of the device to prevent motion of one or more of the bone fragments around the device. When metallic devices are used, screws, pins and sliding nails are used to achieve this fixation. Another method, taught in Berger, U.S. Pat. No. 5,658,310, involves anchoring the balloon portion of a balloon catheter in the medullary cavity at one end of a long bone having a transverse fracture, and stretching the remaining portion of the elastic catheter across the fracture interface within the bone to maintain the fracture interface in compression. It would appear that unless the elastic catheter traverses the precise center of the bone at the fracture site, compressive forces will be uneven across the fracture site. That is, the compressive forces on the side of the bone nearest the catheter will be greater than the compressive forces on the opposite side of the bone, generating an unwanted bending moment across the fracture site. Furthermore, a primarily compressive repair is not able to buttress multiple fragment or share loading as is required to stabilize comminuted fractures, limiting the usefullness of the method to a specific class of simple fractures.

Surgical procedures used to mount bone plates and cerclage elements to a bone often require supportive tissue that is normally joined to the bone to be cut from the bony tissue to enable direct visual access to the bone. With cerclage procedures, one must entirely encircle a bone in order to hold the bony parts together.

Procedures using bone plates and cerclage elements also often tend to interrupt blood flow to the damaged bone fragments, and thus hinder the healing process. Moreover, the use of rigid bone plates and intramedullary rods especially with locked screws can lead to stress shielding of the fracture site. It is well known (Wolffs law) that bone growth is stimulated when stress is applied. However, continuous, excessive pressure applied to a bone can cause unwanted resorption of bone at the pressure site. In order to promote healing of bone fractures, the fracture surfaces that are brought together during reduction of the fracture should be subject to cyclic or periodic compressive forces so as to stimulate the growth of new bone across the fracture interface without causing bone resorption. When a fracture interface is immobilized, as by a cast, the bone material that is deposited at the fracture interface may have a collagen fiber matrix that is random rather than aligned with the fiber matrix of bone on either side of the fracture, the healed fracture interface being weaker in tension than bone on either side of the interface.

Some bone fractures result in the production of many bone fragments, and proper reduction of the fracture requires the fragments to be carefully reassembled next to each other with their fracture surfaces in contact. Bone screws and bone plate devices commonly are used for this purpose. Using bone screw techniques, two bone fragments may be joined together, and these two fragments as a unit may be moved into approximation with a third fragment and joined to it, and so on. Fragments that are thus joined together by rigid screws cannot move with respect to other fragments, and mismatching of the fracture surfaces as the first several fragments are joined together can have a compounding effect, causing malunion or non-union of fracture surfaces and resulting in far less than perfect bone fragment assembly and healing.

As such, articular and comminuted fractures generally require special attention to create a repair construct stable enough to allow early mobilization, but not configured and assembled in a manner which causes stress shielding.

Stress shielding results from force transfer through the implanted stabilization device verses the bone fragments. This situation is exacerbated when bone fragments are held apart by the fracture repair implants. Appropriate reduction of fracture fragments is more important when more rigid "locked" fixation devices are employed as excessive stress-shielding can result in a non-union. The optimal results are achieved when: (1) normal bone anatomy is reconstructed; (2) a portion of the physiologic force is directly transmitted through the bone; and (3) the bone fragments are reassembled and supported in a manner that the fragments, and particularly any articular surface fragments, move less than about 1 to 2 mm in the early post operative stages while callus and/or bone are being formed.

Successful use of flexible plating techniques in unstable fracture patterns is dependent, in part, on the use of a combination of devices such that each fracture fragment is stabilized via direct fixation, buttressing or force neutralization.

When dealing with plating systems the placement of multiple screws on each side of the fracture can distribute of loading between more than one screw on either side.

Stabilization of a fracture requires prevention of translation in all three directions and rotation about all three axes. Restraining a point solves translation but not rotation. Plates provide some rotational stability. The best mechanical advantage is obtained during fixation when plates (or screws) are not placed along the same axis.

A range of fasteners are needed create rigid constructs which can provide mechanical stability to an injured skeletal structure, and yet facilitate optimal healing. Among the commonly used stabilizers are internal and external fasteners such as headed bone screws, pitch differential bone screws, bone screws with lag fragments, bone screws and pegs which, when locked to plates or rods, buttress fragments, bone bolts, bone nails, bone pins, bone plates, rods, rod connectors, cables, wires, external and adjustable fixators, et cetera.

Infractures in metaphyseal and epiphyseal bone, a single-sided internal fixation construct using non-rigid connections to plates or rods can not provide sufficient stability to prevent undesirable motion under non-resistance loading or passive motion, let alone normal functional loads. This is particularly applicable when pathological bone or comminution is encountered, and in certain juxta articular impaction fractures (e.g. a die punch fragment), In many cases appropriate stability can only be achieved by use of constructs with a combination of features such as rigid or semi-rigid connections (locked pegs or screws, unilateral motion as in sliding compression hip screw or sliding spinal plates), or use of multiple plates and fasteners or nails and fasteners.

Aptus by Medartis International (Germany) provides a fastener that retains its position through a surface wedge fit, relying on surface friction. This device, however, provides minimal material interference to resist pull out or pull through.

In U.S. Pat. No. 6,955,677 Dahners discloses the use of spherical threads on screws which tap in to a softened or compliant region of a plate which has been "disposed" on the inside surface of the aperture to facilitate this tapping.

SUMMARY OF THE INVENTION

The disclosed fasteners have a expansion head to secure the fastener in a support structure. The expansion fastener has a removable locking ring, a head, and a shaft extending from the distal end of the head. The exterior of the head has at least one slot extending, extending partially or fully, from the edge toward the distal end. In one embodiment the locking ring has an outer periphery, at least one tab that extends beyond the periphery and a tool receiving area.

The head is substantially cylindrical with a proximal end, middle section and a distal end. The proximal end has an open area with an edge, a base and a first diameter. The distal end has a tool receiving area and a diameter less than the diameter of either the proximal end or middle section. The middle section has a tool receiving area that is contiguous with the open area of the proximal end and a diameter greater than the distal and proximal ends.

A channel is formed along the periphery of open area by a top rim and the base having a channel wall. The interior diameter of the top rim is dimensioned to receive the outer periphery of the locking ring and at least one tab receiving area within the top rim is dimensioned to receive the locking ring tabs. There is a wall periphery reduction, preferably gradual to control expansion, adjacent to each of the tab receiving areas. The rotation of the locking ring to place the tabs in contact with the wall periphery reduction causes the exterior of the head to expand at the slots.

The exterior of the head can be smooth or have at least one thread having a height and a depth and extending from and around head. The thread can be perpendicular to the axis of the shaft; have parallel ridges to the axis of the shaft; or be perpendicular to the axis of the shaft. The shape of the head can be spherical with spherical threads or torroidal with torroidal threads. Alternatively the exterior of the head can be cross-hatched or a combination of the above.

The expansion fastener head can also have at least one flat extending from the proximal end to the distal end of the head as well as a cutting flute, adjacent one or more flats.

In another embodiment the locking ring is secured to the interior of the head by threading. The tool receiving area can be recesses or other applicable means. The locking ring has a treaded outer periphery and a tool receiving area. The interior of the substantially cylindrical head has a diameter that decreases from the edge to the base with a thread pattern matching the thread pattern of the locking ring. As the locking ring is threaded deeper into the decreasing interior diameter of the head, the exterior of the head expands at the slots.

To use the disclosed fastener to secure biological material to a support material it is preferably, although not mandatory, that the locking ring be placed into the expansion fastener head. The biological material, such as bone or tissue, is aligned with the support material, such as a plate, bone or other tissue. If holes are required they would be drilled and the material realigned. The fastener threaded shaft is threaded through the support material and into the biological material. Once in place, the locking ring is rotated to expand the head, thereby locking the fastener in place.

BRIEF DESCRIPTION OF THE DRAWINGS

The preferred embodiments of the present invention are shown by a way of example, and not limitation, in the accompanying figures, in which:

FIG. 1 is a side perspective view of a smooth outer diameter split head fastener in accordance with the disclosure;

FIG. 2 is a side perspective view of a threaded outer diameter split head fastener having flats in accordance with the disclosure;

FIG. 3 is an enlarged view of the fastener of FIG. 1 in accordance with the disclosure;

FIG. 4 is an enlarged view of the fastener of FIG. 2 in accordance with the disclosure;

FIG. 21 is a cut away of the screw of FIG. 10 having interior threads with the locking ring inserted in a no load position, in accordance with the invention;

FIG. 22 is a cutaway side view of the slotted head of FIG. 10 with the locking ring rotated to provide increased load in accordance with the invention;

FIG. 31 is a cross sectional side view of the cannulated expansion tool inserted into a two slot, smooth OD split head fastener in accordance with the disclosure;

FIG. 32 is a perspective view of a split lock fastener with a driver bit and expansion tool in place in accordance with the invention;

FIG. 33 is a side view of a split lock screw on a driver in accordance with the invention;

DETAILED DESCRIPTION OF THE INVENTION

Definitions

Figure 5:
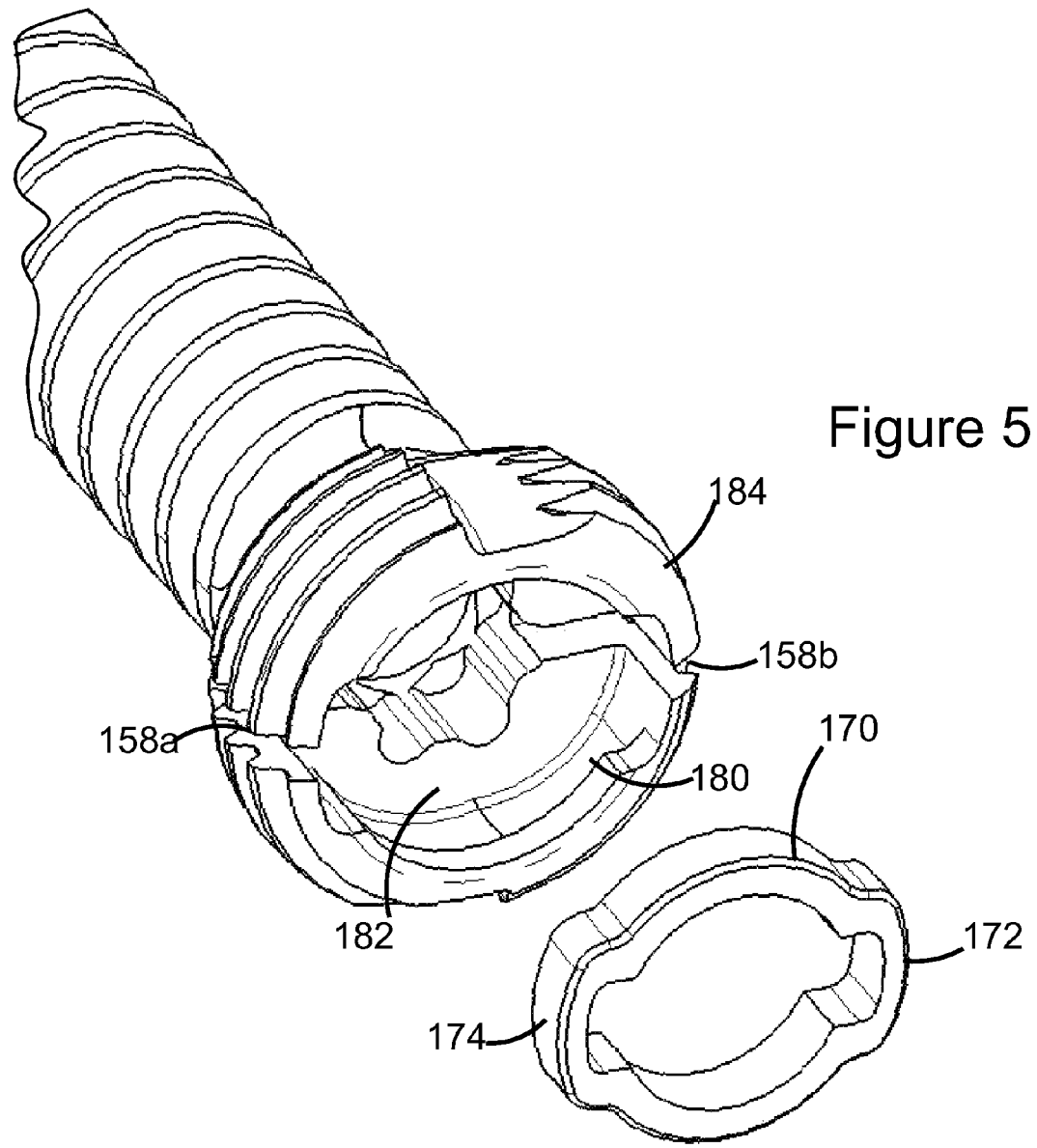
FIG. 5 is an end perspective view of the fastener of FIG. 2 with the locking ring clearly separated from the head of the fastener, in accordance with the disclosure.

Where the definition of terms departs from the commonly used meaning of the term, applicant intends to utilize the definitions provided below, unless specifically indicated.

For the purposes of the present invention, the term "aperture surface" refers to any surface, organic or manufactured from natural or synthetic material, to which the head of the fastener is attached.

For the purposes of the present invention, the term "plate" refers to a piece of material with greater width and height than thickness, e.g. a thin piece of material. The plate can be flat, angled or curved and can have one at least one hole or groove channel to facilitate use with a fastener.

For the purposes of the present invention, the term "Osteosynthesis" refers any surgical procedure that stabilizes and joins the ends of fractured (broken) bones by mechanical devices such as metal plates, pins, rods, wires or screws until healing occurs.

For the purposes of the present invention, the term "slit(s)" and "slots(s)" are used interchangeably and refer to the spacing between sections of the fastener head the enable the fastener to expand.

For the purposes of the present invention, the term "pathologic bone" includes but is not limited to osteoporotic bone, osteoporotic vertebral bodies, fractured osteoporotic vertebral bodies, fractures of bones due to tumors especially round cell tumors, avascular necrosis of the epiphyses of long bones, especially avascular necrosis of the proximal femur, distal femur, distal radius and proximal humerus and defects arising from endocrine conditions.

For the purposes of the present invention, the term pitch differential (Total PD) refers to the number of screw threads on the head multiplied by individual pitch differences. E.g. If pitch differential is 0.1 mm, the Total PD is 0.1×3=0.3 mm for the 3 threads.

For the purposes of the present invention the terms "sphere" and "spherical" as employed herein are not limited to exact spheres or spherical contours. The terms are intended to include hole contours that are of progressively decreasing diameters from the proximal end of the hole to the distal end of the hole. The progression forms a curved line and thus a conical contour is outside of the scope of the terms sphere and spherical.

For the purposes of the present invention, the term "fastener" refers to any device that joins or affixes two or more objects together.

For the purposes of the present invention, the term "flute" refers to a channel, groove, or furrow, on the body of the fastener head, or recessed regions below the spherical surface of the fastener head, that are provided specifically to facilitate tapping or cutting. The flutes can be cut to form a cutting edge at one edge. A flute's recessed region can have various shapes, but in all cases, a cutting edge or cutting lip is retained at one edge. Preferably, a flute in axial alignment with the shaft of the fastener body. Preferably, the shaft is threaded at an angle which is different from the angle of the threads of the fastener head.

For the purposes of the present invention, the term "flat" refers to a recessed region (below the fastener head) that does not feature a cutting edge or cutting lip. Flats can take on multiple shapes which include a truly flat surface, a convex surface or concave surface or a combination or recessed surfaces.

For the purposes of the present invention, the term "grooved", "grooves" or "groove" refers to any channel, valley or path in the fastener surface, including but not limited to spiral, circular, oblong, as well as any other pattern that provides the desired result set forth herein, that forms the threads.

For the purposes of the present invention, the term "threaded", "threads" or "thread" refers to the material between grooves. Preferably, a flute is in axial alignment with the shaft of the fastener body. Preferably, the shaft is threaded at an angle which is different from the angle of the threads of the fastener head.

Although the use of threaded-head screws has provided improvements in orthopedic surgical techniques, this method of retaining a screw in a plate is not applicable in all situations.

The disclosed fasteners use expansion, with or without additional locking through the use of treads, to retain a screw within a plate. When used with a plate having appropriately sized openings, the disclosed fastener mechanically locks to the plate in a manner to prevent the fastener from moving from the affixed position. Once expanded, the fastener will not rotate, slide pull through or back out of the opening. The disclosed design uses mechanical expansion to create surface pressures and a friction lock. Alternatively, depending upon the materials being used, the disclosed fastener can deform the surface of the bone or plate resulting in another form of mechanical fit. The residual surface tension and/or interference prevent motion of the fastener head at the expansion junction.

The disclosed fastener can be used to affix plates to bone, bone to bone or tissue to bone. The appropriate materials can be dependent upon the application and will be known to those skilled in the art.

Although prior art expansion fasteners are known, they have heretofore used threading to create the expansion. These have the disadvantage in that debris, such as bone, blood and/or tissue can make the mating of threads difficult. The disclosed system has overcome this disadvantage through the use of an internal expansion ring which, using a cam effect, forces the fastener head to expand when twisted.

Expansion is created by a cam effect using an internal expansion ring which when twisted forces the sides of the split, or slotted, fastener head to expand and engage the mating plate surfaces. At least one cam lock surface is required, but optimally 2 or more cam-lock surfaces are incorporated. In this embodiment, the fastener head has an undercut groove that has a cam surface and openings for the lock tabs of the cam lock ring to pass into the groove during assembly. The openings and tabs are sized such that the tabs snap into the fastener head and are retained within the fastener head. The cam is sized to effect expansion as the cam lock ring is turned.

In each of the embodiments shown, the expansion member is a ring that is preferably pre-installed into the fastener head. The ring preferably is sized to allow the fastener insertion into the plate or bone with the ring in place. For example, this allows the screw to be driven with the cam lock or thread lock in place. A second component does not have to be assembled to the screw to cause expansion after the screw has been installed and is within the surgical wound space. However a less preferred embodiment would include a dam ring that was either solid or whose center opening was not large enough to allow the screw driver tip to engage the screw while the cam lock is in place. This cam lock would be secondarily installed into the fastener head to cause the expansion lock to the plate holes.

The figures hereinafter illustrate the locking ring in different positions in a variety of embodiments. It should be noted that the movement and positioning of the locking ring occurs the same regardless of the exterior configuration of the head or the number of tabs. Figures have been incorporated that illustrate the progression for one embodiment, however not all embodiments have been illustrated in each of the separate positions of the ring.

As illustrated herein the tool receiving areas are recesses within the locking, either in the top or within the inner circumference. It should be noted that the tool receiving areas can be any design that will receive the appropriate tool including, but not limited to, slots, holes, or protrusions. Additionally, a single tool, or multiple tools, can be used to insert the fastener. A tool, as illustrated herein, can be used to place the fastener and a second tool used to rotate the locking ring. Alternatively, a single tool having a distal portion for positioning the fastener and a proximal portion that interacts with the locking ring once the fastener is placed.

In FIGS. 1 and 3 the fastener 100 the outer surface of the head 102 is smooth with four slots 108a, 108b, 108c and 108d. As can be seen in these figures, the slots 108a-108d are evenly spaced from one another around the head 102 and extend along the sides of the head 102 almost to the threaded shaft 104. The proximal end 110 of the head 102 is open with an top rim 126 that has been dimensioned to receive the locking ring 120. The top rim 126 has receiving areas 116 and 118 to receive locking ring 120 tabs 122 and 124.

The periphery of the channel formed by the top rim 124 and the base of the open area gradually narrows, as illustrated in more detail hereinafter, to create the expansion when contacted by the tabs 124 and 122.

In FIG. 3 it can clearly bee seen how the tabs 122 and 124 of the locking ring fit into the receiving areas 116 and 118 at the initial stage of insertion.

The external surface of the disclosed fasteners herein can be smooth or ridged. The ridges of different forms are used to facilitate motion resistance in differing directions, particularly if, during the expansion process, the ridges of the fastener head are deformed into the surface of the plate or bone.

The ridges will generally follow the shape of the spherical or torroidal surface of the fastener head and may be one of several forms.

(A) Circumferential rings perpendicular to the axis of a shaft to prevent rotation of the fastener head relative to the plate or bone under cantilever loading.
(B) Linear ridges which are generally parallel to the axis of the shaft to prevent rotation about the axis of the fastener.
(C) Spherical threads on a spherical surface or torroidal threads on a torroidal surface.
(D) Cross hatch pattern to prevent rotation about the axis of the fastener.

When the ridges on the external surface are helical threads, they can be sized such that the threaded peaks protrude or extend beyond the sizing of the mating surface in the plate or the bone. In this case, the thread can be tapered as in the tip of a wood screw to cut a thread into the mating surface. Alternatively one or more flats or one or more cutting flutes can be cut to facilitate thread engagements. In this manner early stability can be achieved with thread interference. This early stability is then enhanced by expansion of the head of the fastener.

Similarly, FIGS. 2, 4, and 5 illustrate the fastener 150 wherein the head 152 has a threaded exterior with flats 160 with threaded shaft 154. The use of threads 156 and flats 160 are described in detail in co-pending application Ser. No. 12/266,210, filed Nov. 6, 2008 the disclosure of which is incorporated herein as though recited in full. In this embodiment the head 152 has two slots 158a and 158b on opposing sides of the head 152 with the flats 160 at a 90 degree rotation from the slots 158a and 158b. In FIG. 4, the locking ring 170 has been rotated approximately 90 degrees, placing the tab 172 under the flat 160 and contacting the decreased diameter within the channel 180 thereby widening the slots 158a and 158b. In FIG. 5, the locking ring 170 has been removed to more clearly illustrate the interior components. The channel 180 can be seen that has been dimensioned to receive the locking ring 170 and receiving areas 162 and 164 to receive the tabs 172 and 174. As can be seen, the locking ring tabs 172 and 174 are dimensioned to match the receiving areas 162 and 164 to enable the locking ring 170 to by pass the top rim and rest on the bottom rim.

The channel 180 is formed by the top rim 184 and the bottom rim, or base, 182 and has a decreasing diameter (as illustrated in more detail hereinafter), therefore forcing the slots 158a and 158b to expand as the tabs 172 and 174 contact the decreased diameter.

Figure 6:
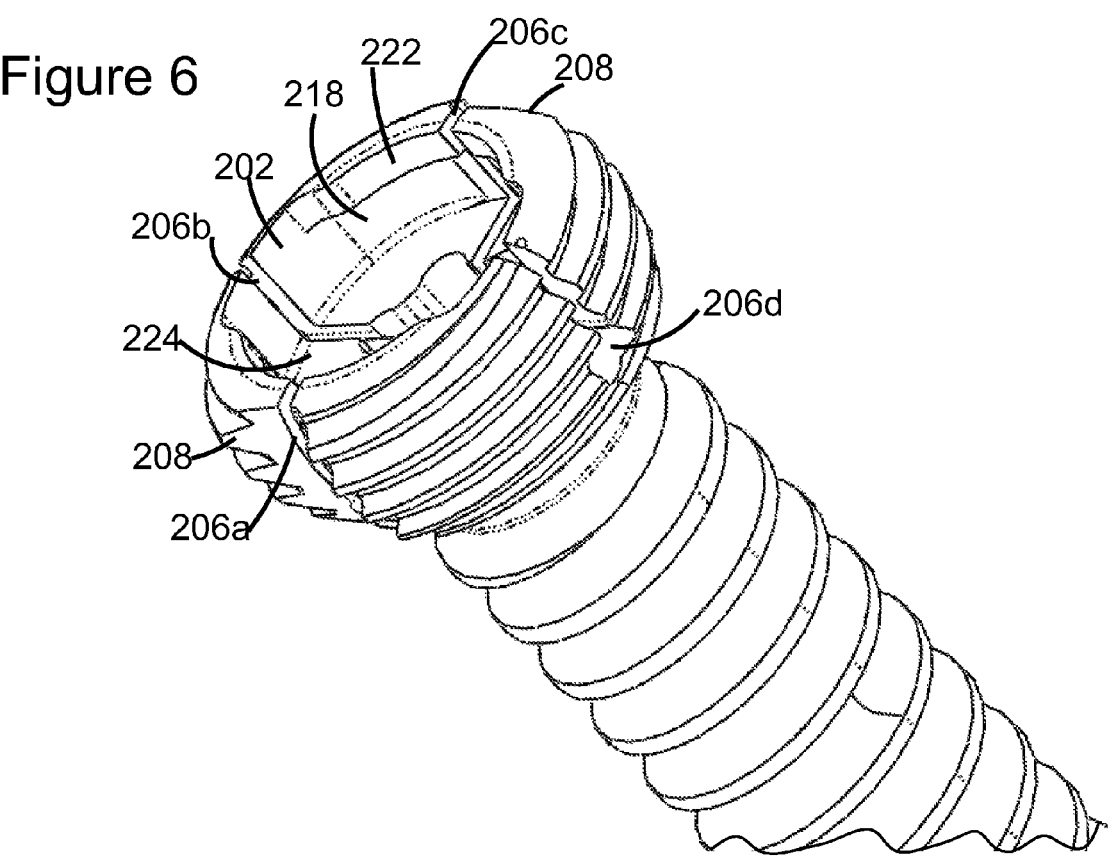
FIG. 6 is a side perspective view of the fastener of a threaded head, four slot fastener having two flats, in accordance with the disclosure.
Figure 7:
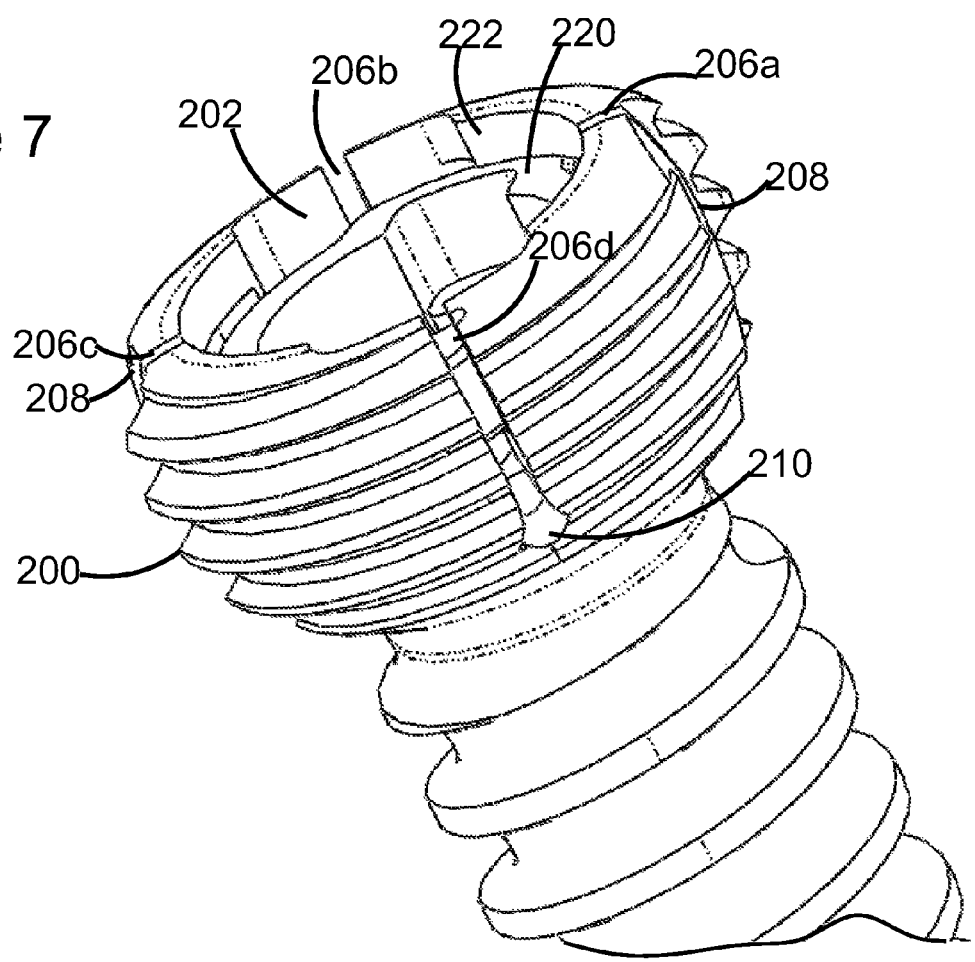
FIG. 7 is a side perspective view of the fastener of FIG. 6 clearly illustrating the four slots and the locking ring receiving area in accordance with the disclosure.
Figure 8:
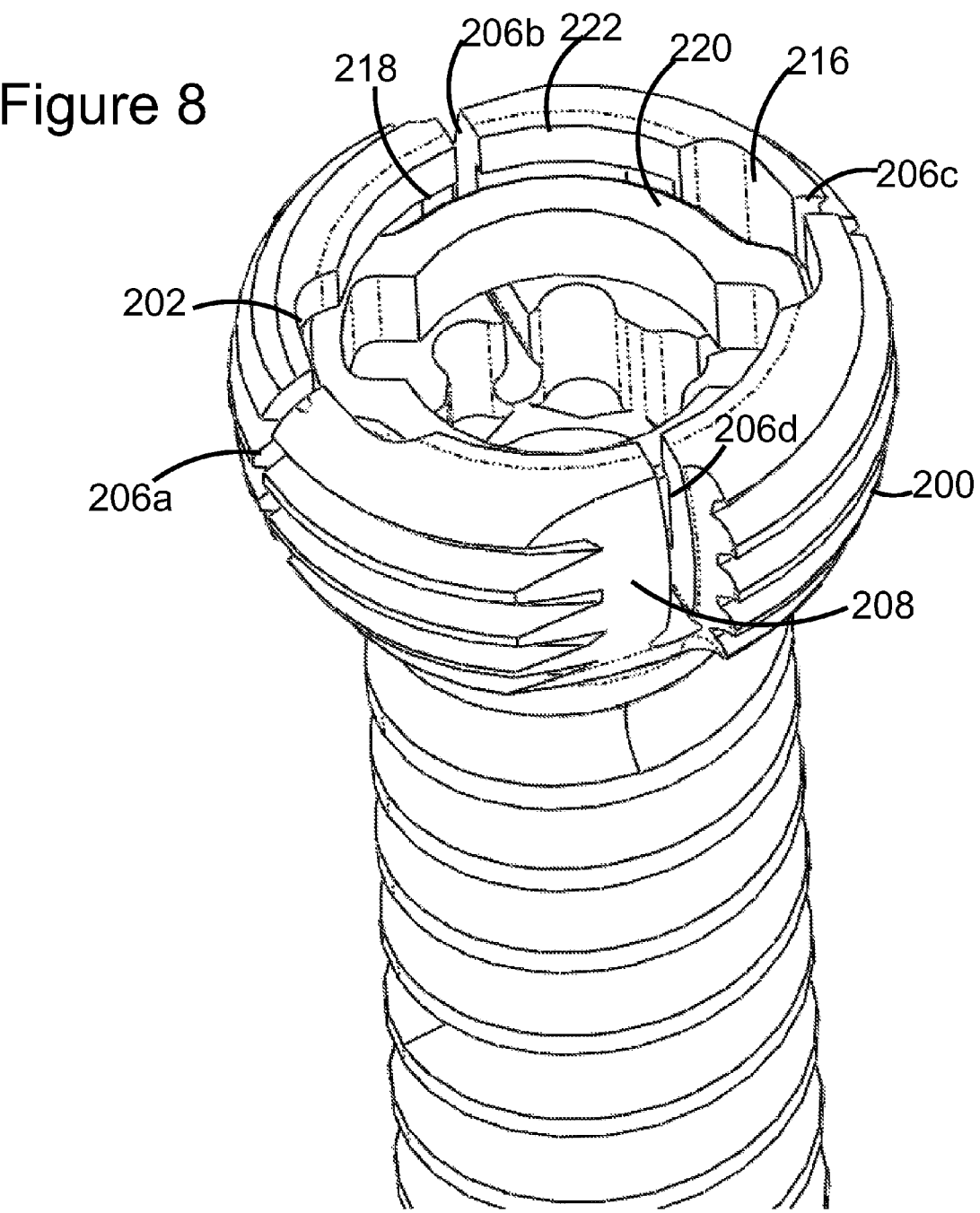
FIG. 8 is a top perspective of the fastener of FIG. 6 clearly showing the flats, in accordance with the disclosure.
Figure 9:
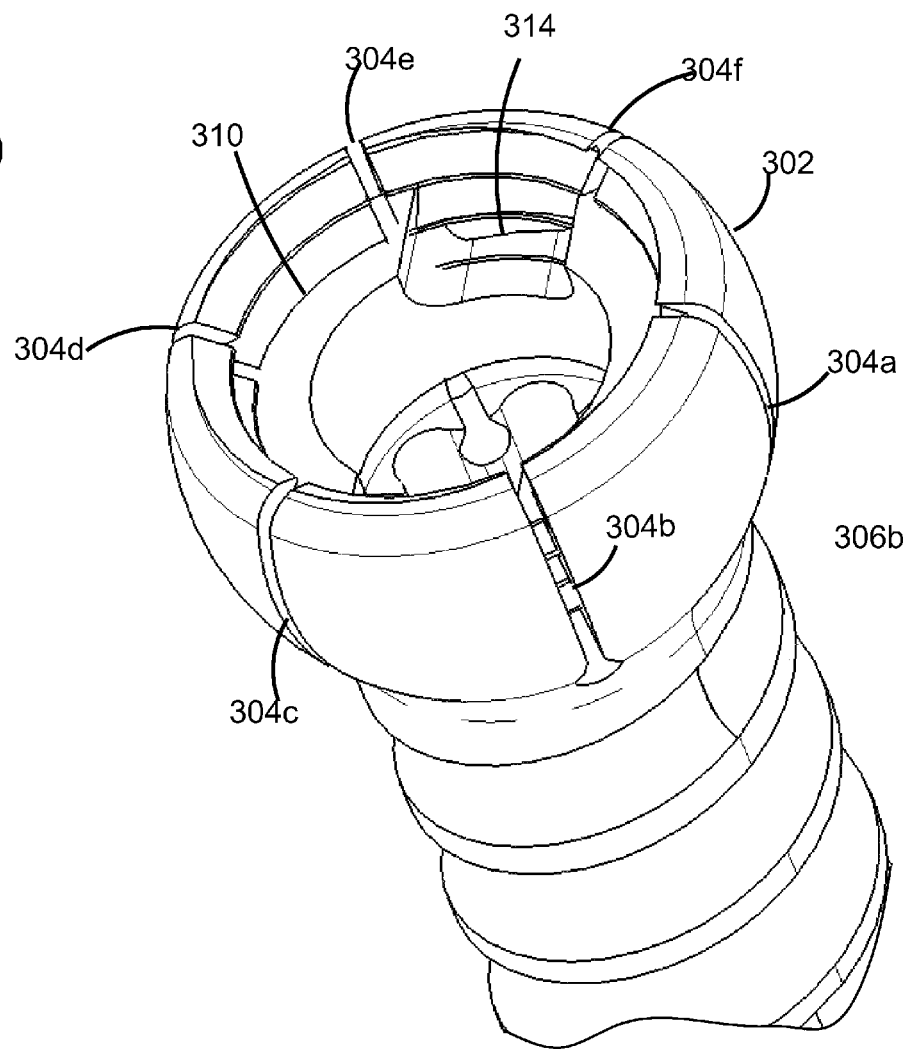
FIG. 9 is a top perspective view of a fastener having a smooth outer diameter and six slits, in accordance with the invention.
Figure 10:
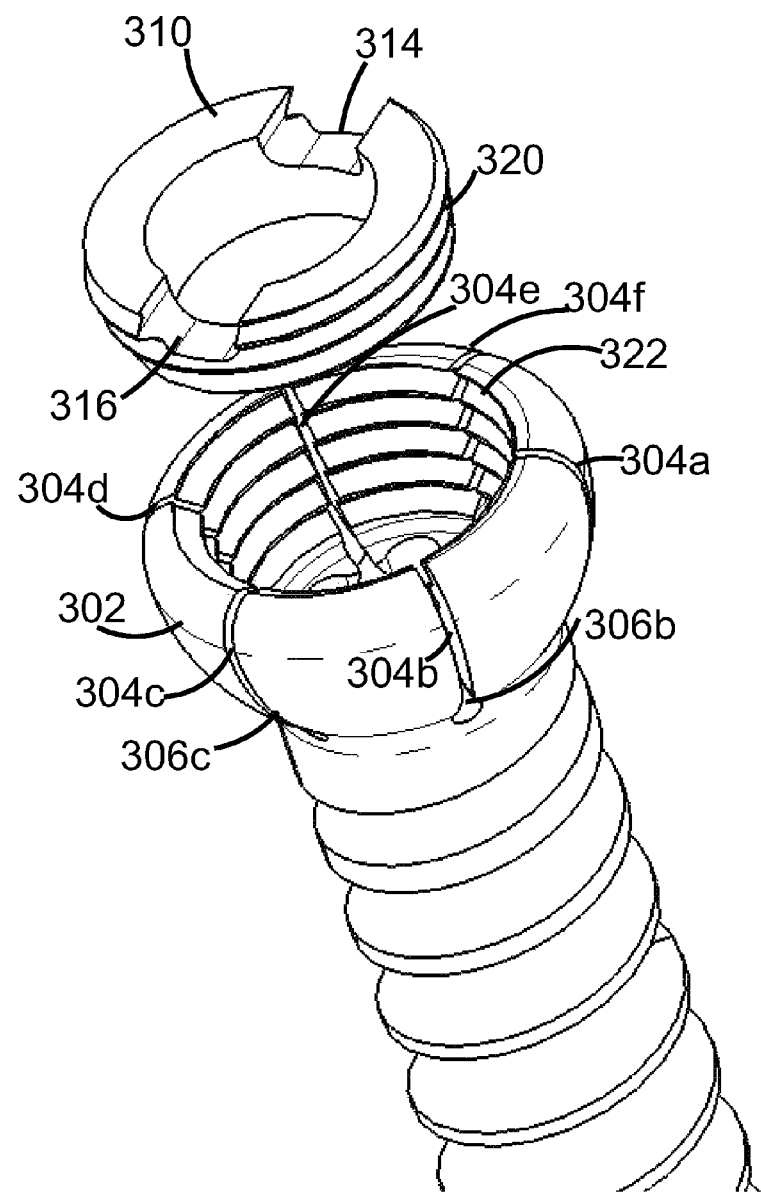
FIG. 10 is an perspective view of the fastener of FIG. 9 with the locking ring separated from the head, in accordance with the disclosure.

The fastener of FIGS. 6, 7 and 8 has a threaded head 200 with four slots 206a, 206b, 206c and 206d, and two flats 208. The upper rim 222 and base 224 are illustrated forming the channel 218. The slots 206a, 206b, 206c and 206d have a keyhole opening 210 (only the opening of slot 206d is illustrated) at the distal end to permit additional expansion without damaging the head 200. In FIGS. 7 and 8 the locking ring 220 was initially inserted with the locking tabs at receiving areas 202 and 216 and resting on the base 224. In these Figures, the locking ring has been partially turned from the insertion position and starting to engage the narrowed interior of the head 200. In FIGS. 9 and 10 the fastener head 302 has a smooth outer surface and six slits 304a, 304b, 304c, 304d, 304e and 304f. Each of the slits 304a, 304b, 304c, 304d, 304e and 304f has an opening 306a, 306b, and 306c (remaining openings not shown) at the distal end to facilitate spreading. In FIG. 9 the locking ring 310 has been inserted into the head 302. As can be seen in FIG. 10 the interior of the head 302 is threaded 322 with a decreasing diameter. The locking ring 310, shown prior to insertion in FIG. 10 and inserted in FIG. 9, has an exterior thread that interact with the threads 322 in the interior of the head 302. The recesses 314 and 316 are configured to receive a locking tool to turn the locking ring 310. As the locking ring 310 is tightened, it forces the head 302 to expand at the slits 304a, 304b, 304c, 304d, 304e and 304f due to the pressure created with the decreasing interior diameter of the head 302.

Figure 11:
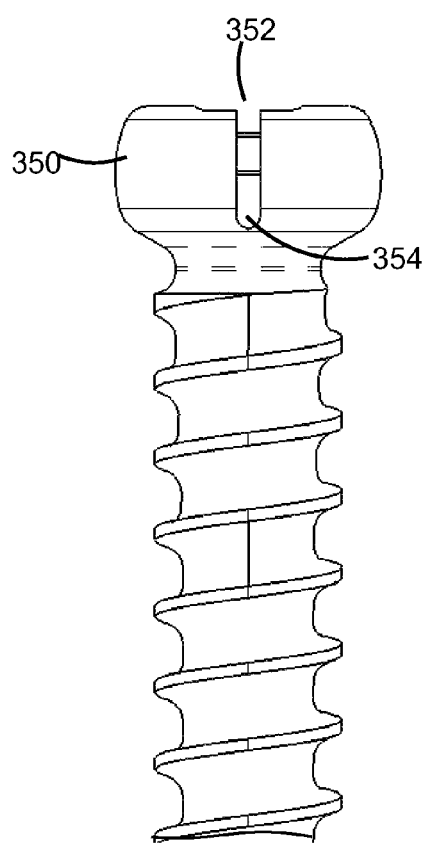
FIG. 11 is a side view of a fastener having a smooth outer diameter head and two slits in accordance with the invention.
Figure 12:
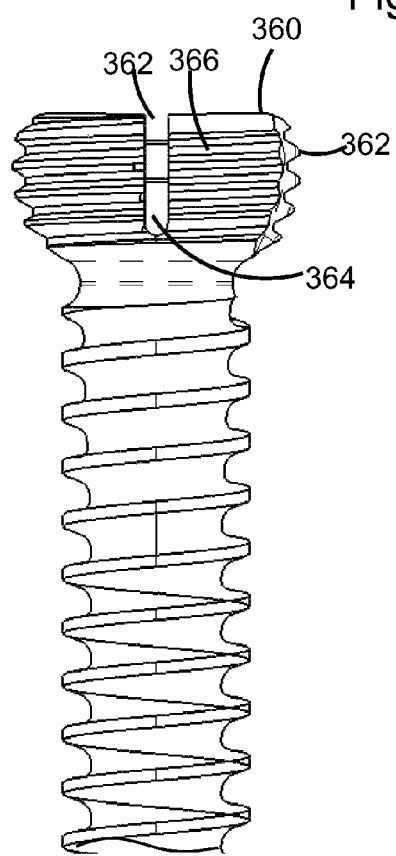
FIG. 12 is a side view of a fastener having a threaded outer diameter head and two slits having curved distal ends, in accordance with the invention.

FIG. 11 is a side view of a fastener head 350 having a smooth outer diameter head and two opposing slits 352 having a curved distal end 354. The curved distal end 354 serves the same purpose as the openings described heretofore. In FIG. 12 the fastener head 360 has threads 362, flats 366 and dual slits 362. As with the design of FIG. 11, the slits 362 have a curved distal end 364.

Figure 13:
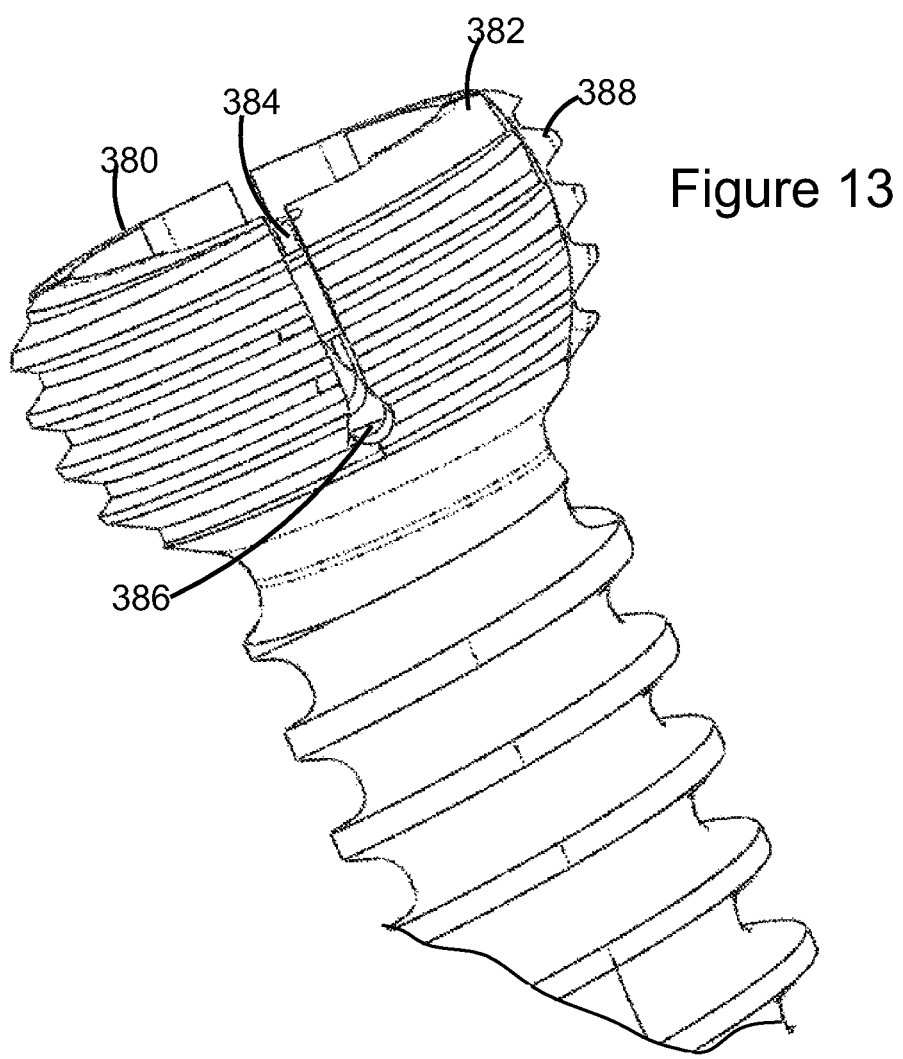
FIG. 13 is a perspective view of the threaded head fastener having slits and flats with a keyhole distal end to the slit, in accordance with the invention.

The head 380 of FIG. 13 has threads 388, flats 382 and two slits 384. The distal end 386 of the slots 384 have a keyhole shape to facilitate spreading of the walls.

Figure 14:
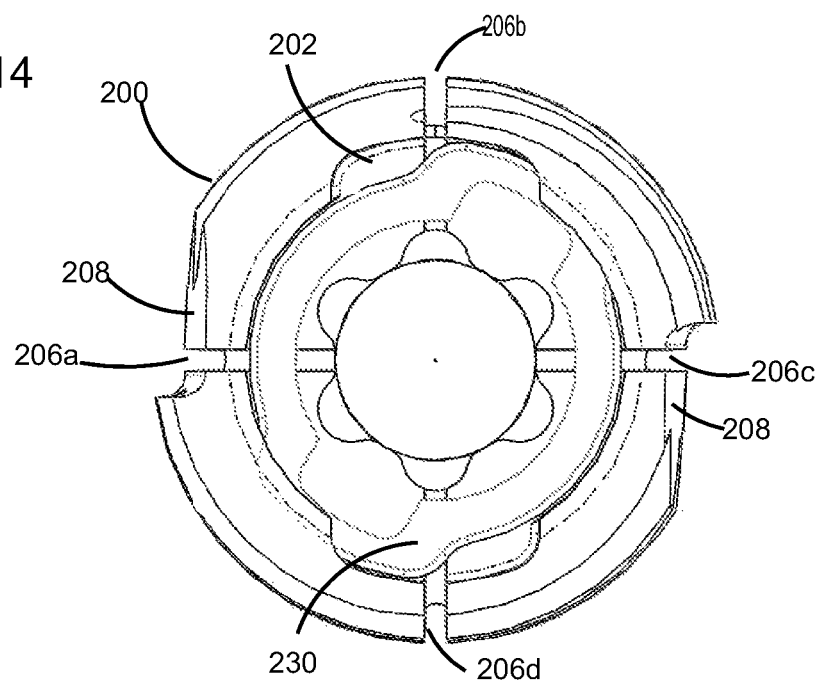
FIG. 14 is a top view of the fastener head having two flats and four slots with the locking ring partially rotated in accordance with the invention.
Figure 15:
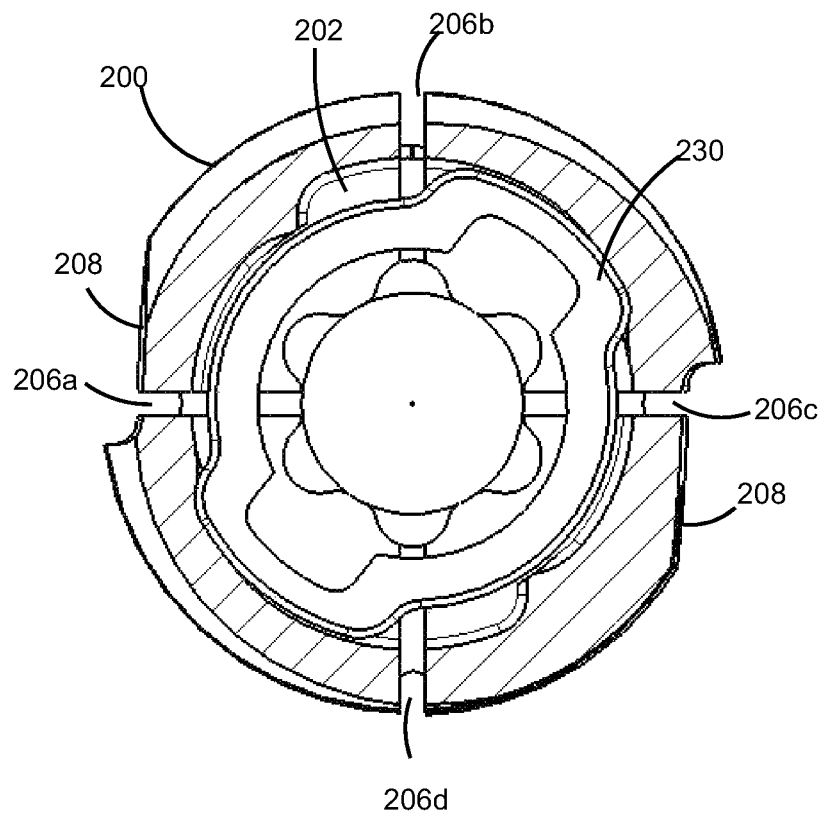
FIG. 15 is a top view of the fastener head having two flats and four slots with the locking ring partially rotated to provide minimal load in accordance with the invention.
Figure 16:
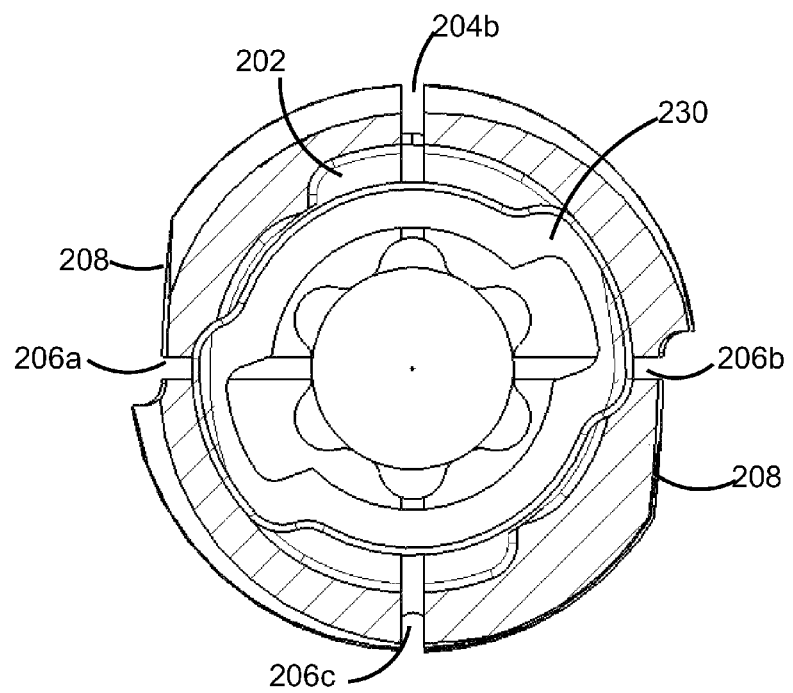
FIG. 16 is a top view of the fastener head of FIG. 15 having increased, but not yet maximum, load in accordance with the invention.
Figure 17:
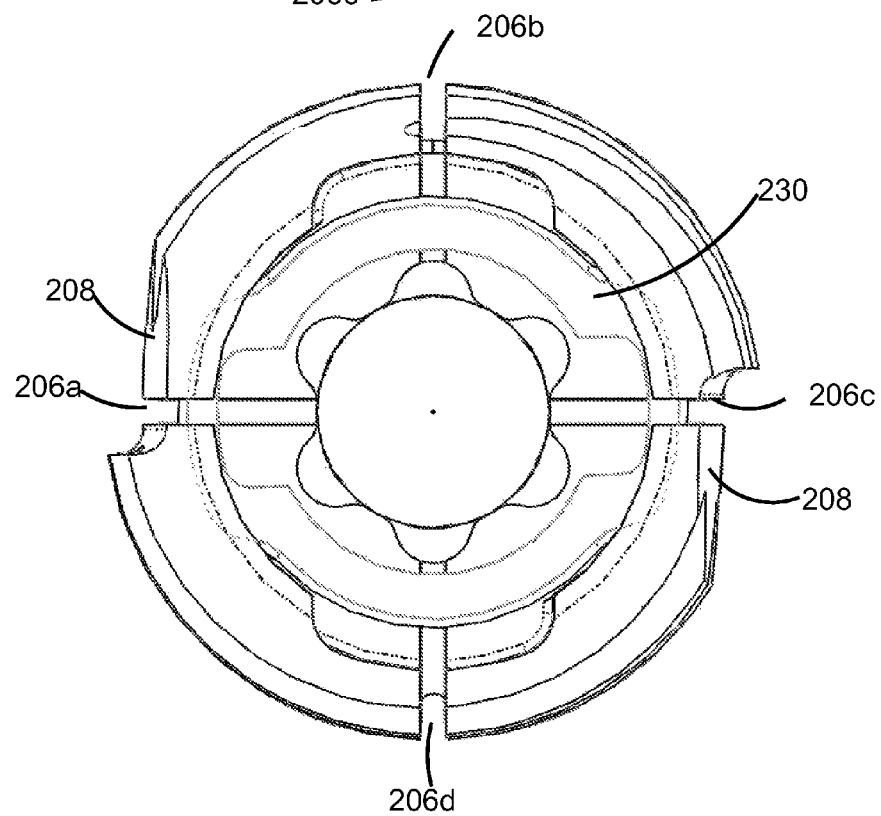
FIG. 17 is a top view of the fastener head of FIG. 15 having maximum load in accordance with the invention.

FIGS. 14, 15, 16 and 17 are top views of the fastener head 200 of FIGS. 6-8 having two flats 208 and four slits 206a, 2064b, 206c and 206d. In FIG. 14 the locking ring 230 has been inserted into the receiving area 202 and partially turned. FIGS. 15, 16 and 17 illustrate different degrees of rotation of the locking ring 230, with FIG. 17 illustrating the maximum expansion position.

Figure 18:
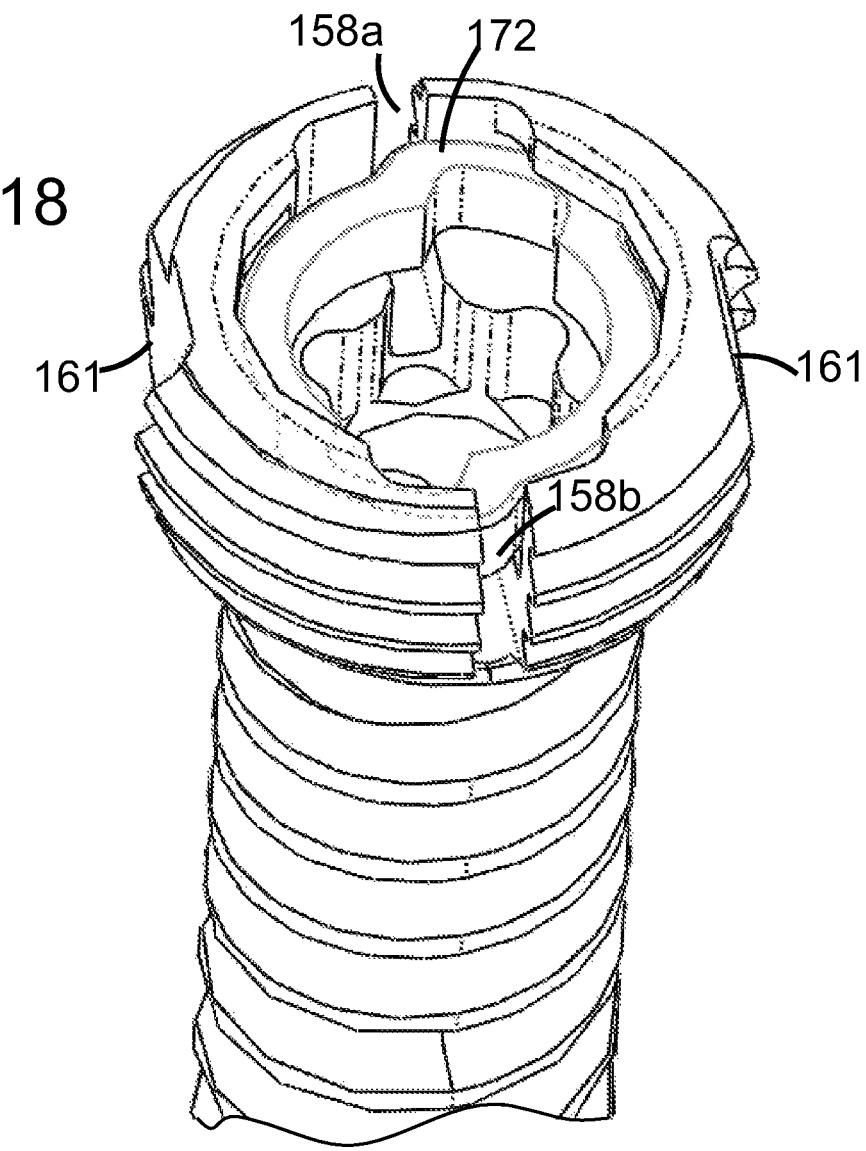
FIG. 18 is a perspective view of the fastener head having two slots with opposing flats with minimum load in accordance with the invention.
Figure 19:
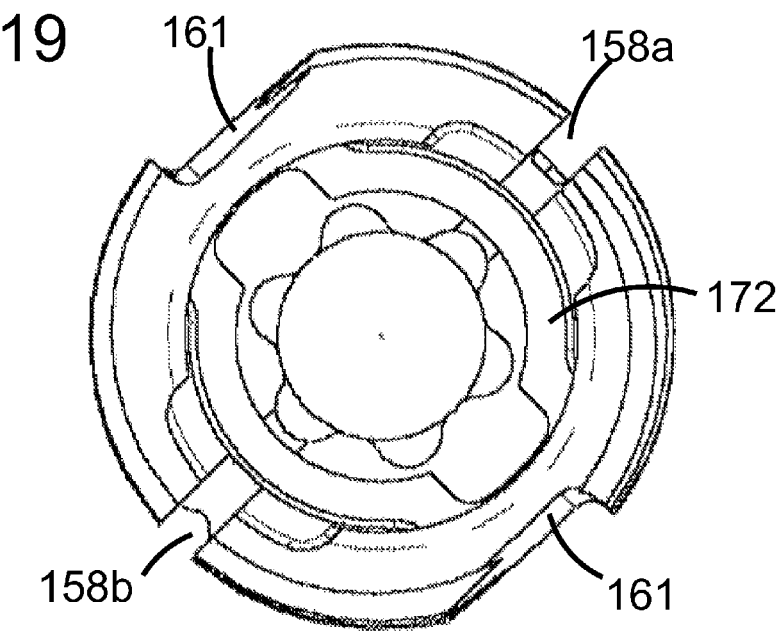
FIG. 19 is a top view of the fastener head of FIG. 18 in maximum load in accordance with the invention.
Figure 20:
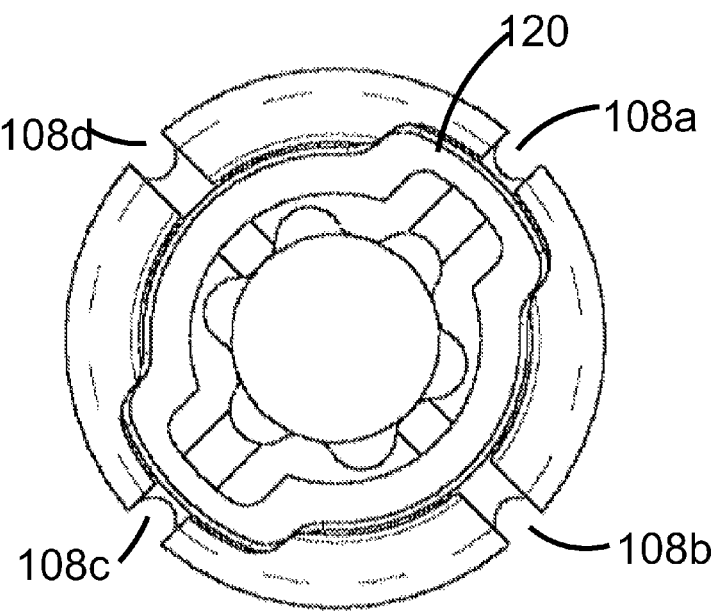
FIG. 20 is a top view of the four slot head having no load in accordance with the invention.

FIG. 18 is a perspective view of the fastener head 150 of FIGS. 2 and 4 showing the locking ring 172 causing minimum load while in FIG. 19 the locking ring 172 has been rotated to cause maximum load. FIG. 20 is a top view of the four slot 108z, 108b, 108c, 108d head of FIG. 1 with the locking ring 120 initially inserted. As noted previously, the rotation of the locking ring and expansion of the head is applicable for all embodiments using the interior channel, whether the exterior is threaded or smooth. Therefore, the insertion of the locking ring 172 would appear the same as the insertion of the locking ring 120.

FIGS. 21 and 22 illustrates, through a cutaway of the screw head, the fastener of FIG. 10. In FIG. 21 the threaded ring 310 has been inserted into the head 302 and engaged with the interior threads 322. In FIG. 22, the threaded ring 310 has been tightened, through use of a tool inserted into the recesses 314 and 316. As described in conjunction with FIG. 10, as the ring 310 is tightened in the decreasing diameter of the head 302, the head 302 expands at slots 306a, 306b, 306c, 3064d, 306e and 306f.

Figure 23:
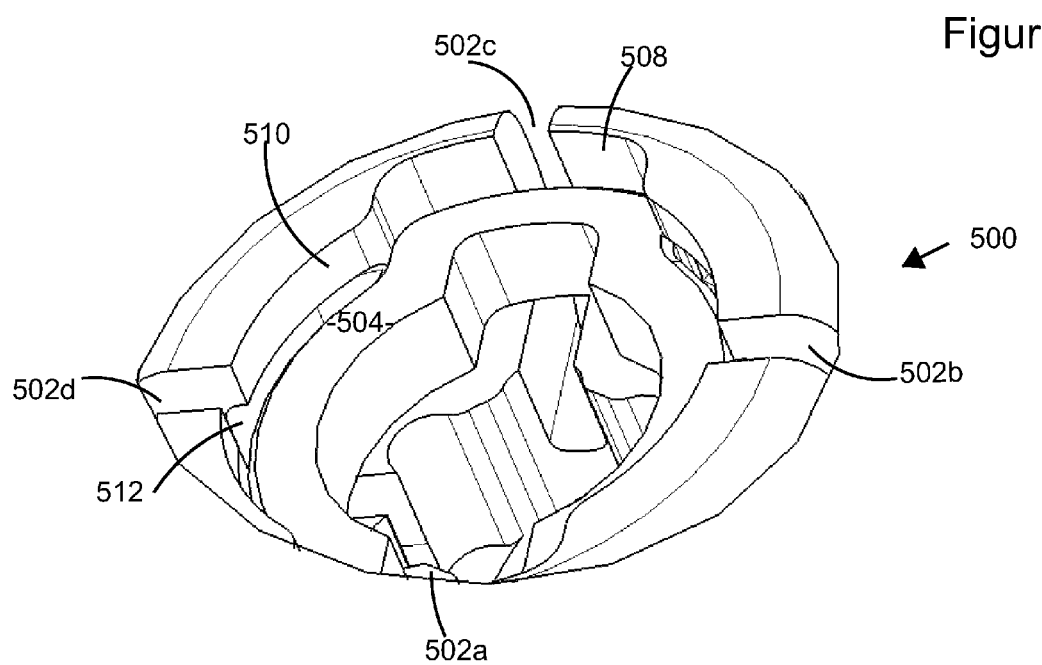
FIG. 23 is an additional perspective view of the four slot fastener head in accordance with the invention.
Figure 24:
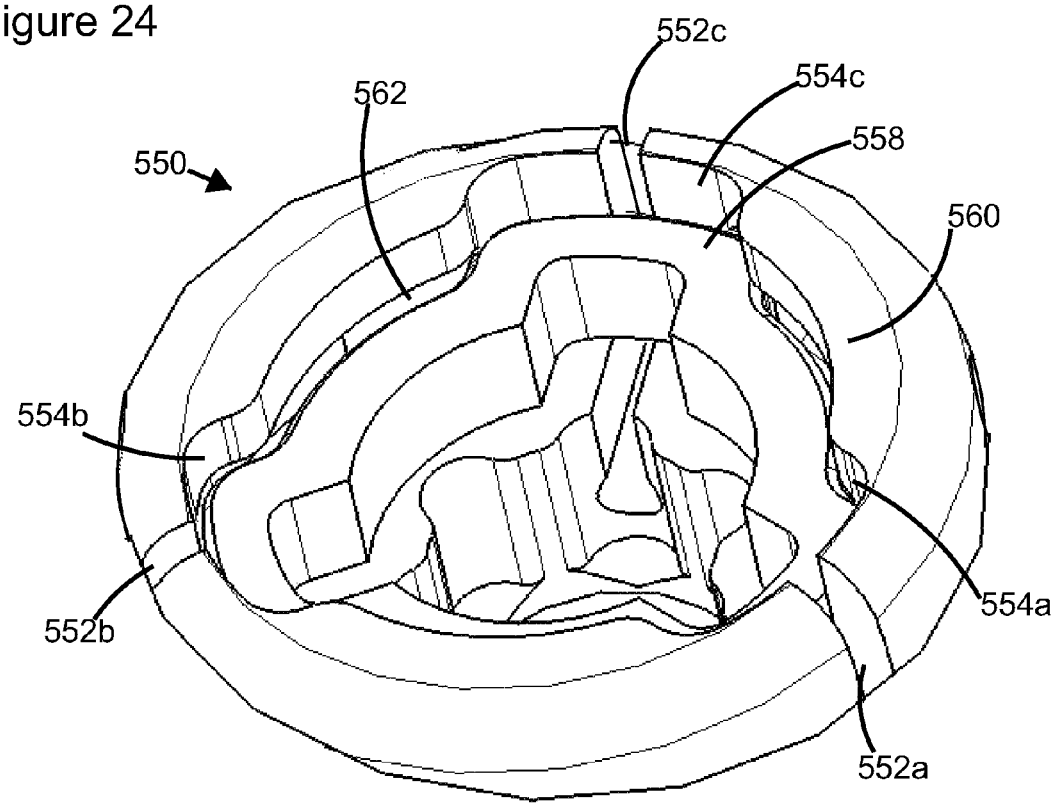
FIG. 24 is a perspective view of a three slot fastener head in accordance with the invention.

FIG. 23 illustrates a head having four slots 502a, 502b, 502c, and 502d with the locking ring 504 inserted into the receiving areas 508. The upper rim 510 is dimensioned to retain the locking ring 504 in the channel 512. is a perspective view of a four slot fastener head in accordance with the invention;

In FIG. 24 the head 550 has three slots 552a, 552b, and 552c with a receiving area 554a, 554b and 554c adjacent to each slot 552a, 552b and 552c. A three tab locking ring 558 is used to expand the head 550. As with the embodiments described heretofore, the locking ring 558 rests on the base of the head 550 (not shown) and is maintained for rotation in channel 562 by upper rim 560.

Figure 25:
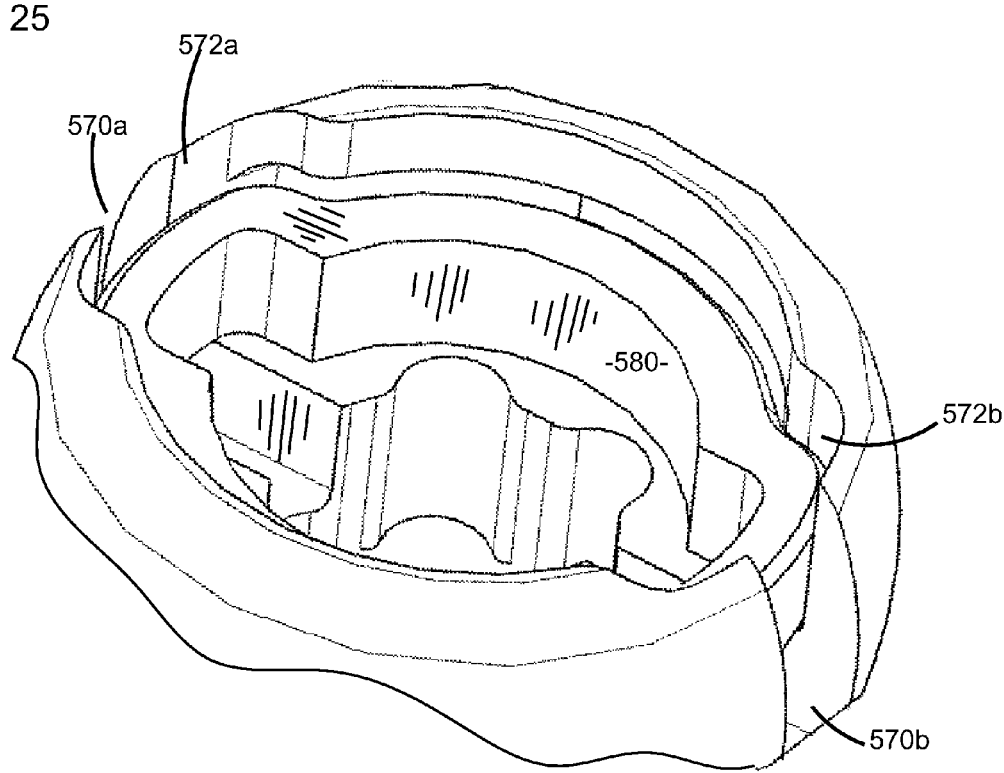
FIG. 25 is a perspective view of a two slot fastener head in accordance with the invention.

FIG. 25 illustrates a head having dual slits 570a and 570b with locking ring 580 inserted into the receiving areas 572a and 572b.

Figure 26:
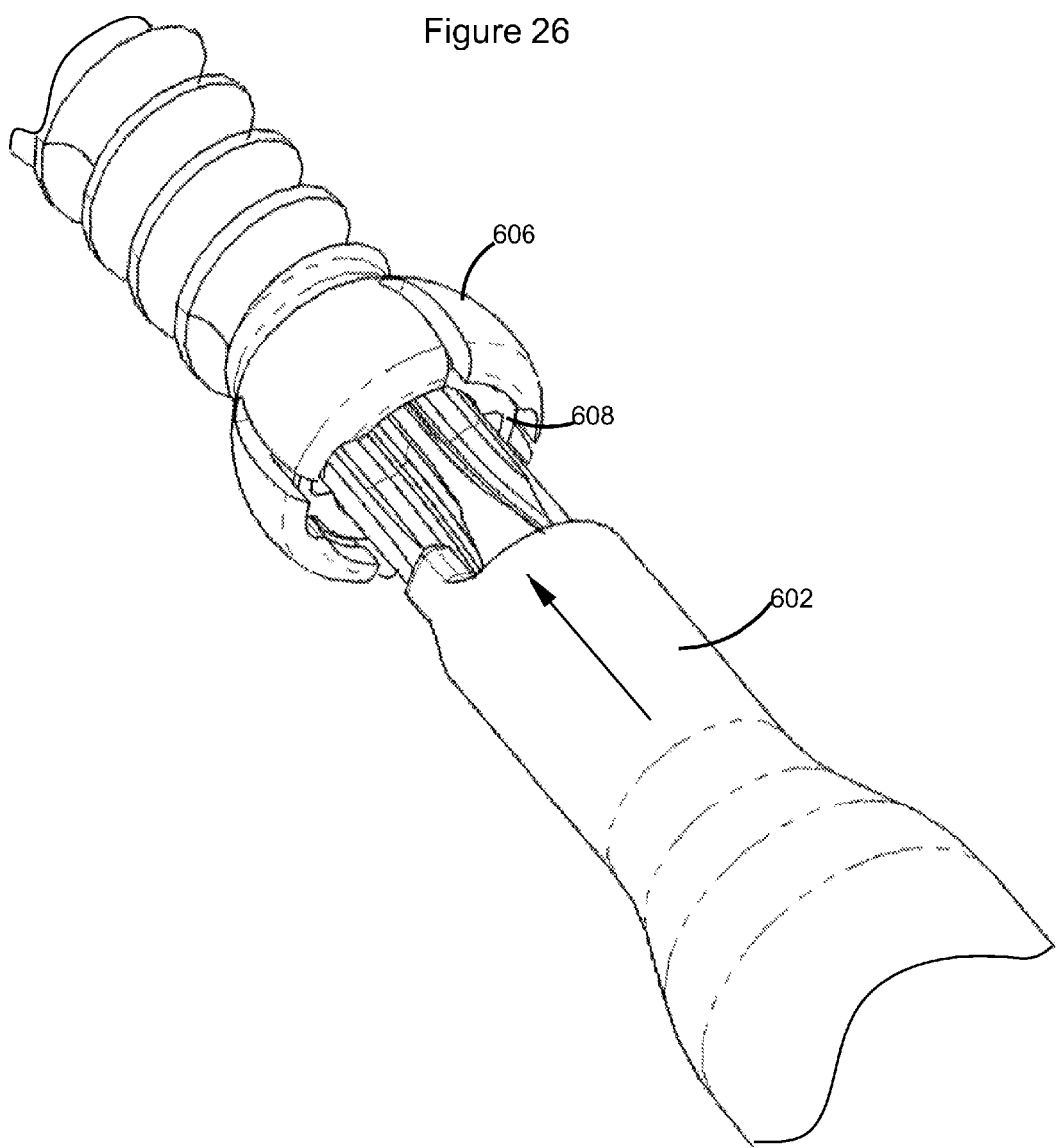
FIG. 26 is a perspective view of a cannulated expansion tool partially inserted into the 4 slot, smooth OD split head fastener in accordance with the invention.
Figure 27:
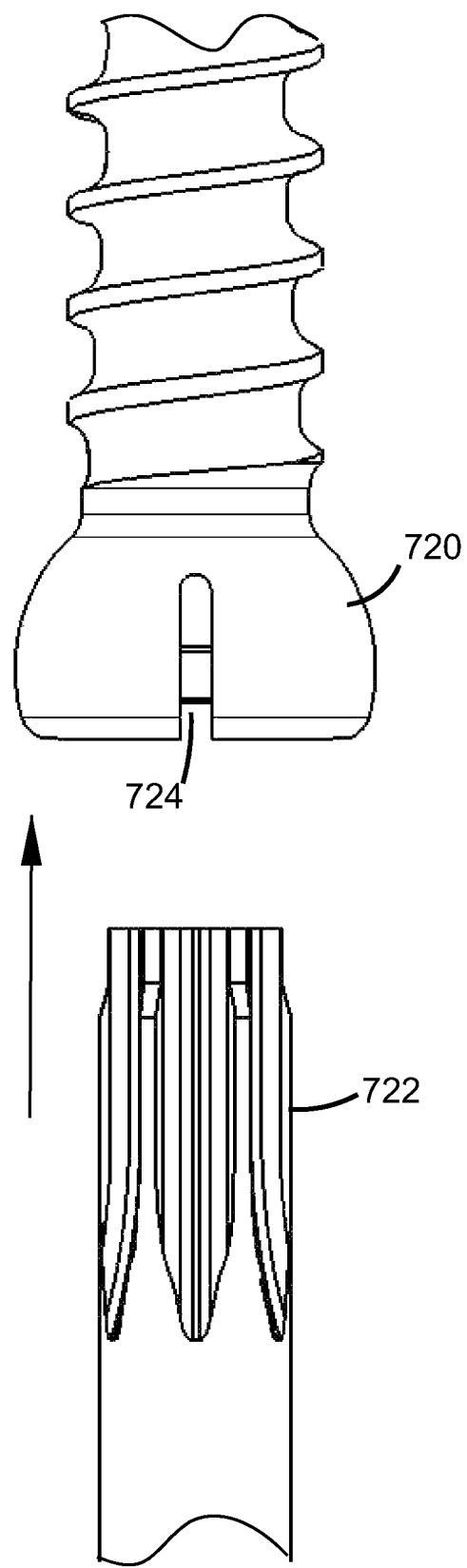
FIG. 27 is a side view of a cannulated expansion tool positioned for insertion into a two slot, smooth OD split head fastener in accordance with the invention.

FIG. 26 show a cannulated expansion tool 602 partially inserted into the head 606 of a four slot, smooth outer diameter fastener. In this figure the locking ring 608 has been inserted into the head 606 and will be engaged once the fastener has been placed FIG. 27 shows a cannulated expansion tool 722 positioned for insertion into a two slot, smooth OD split head fastener 720 having a curved distal end slot 724.

Figure 28:
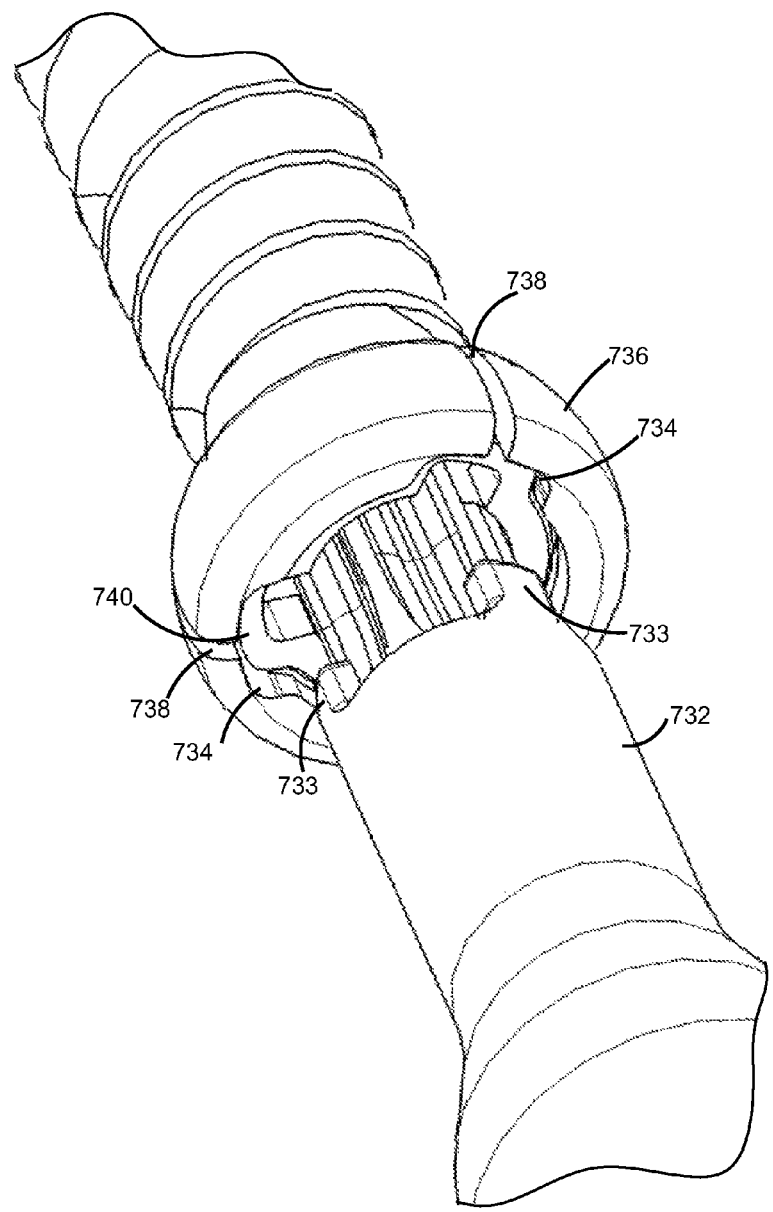
FIG. 28 is a perspective view of a cannulated expansion tool inserted into a three slot smooth OD split head fastener aligned with the locking ring in accordance with the invention.

In FIG. 28 the smooth surface head 736 has three slots 740, having the three receiving areas 734 and a three tab locking ring 740. The insertion tool 732 has three flanges 733 to engage each of the locking ring tabs 738.

Figure 29:
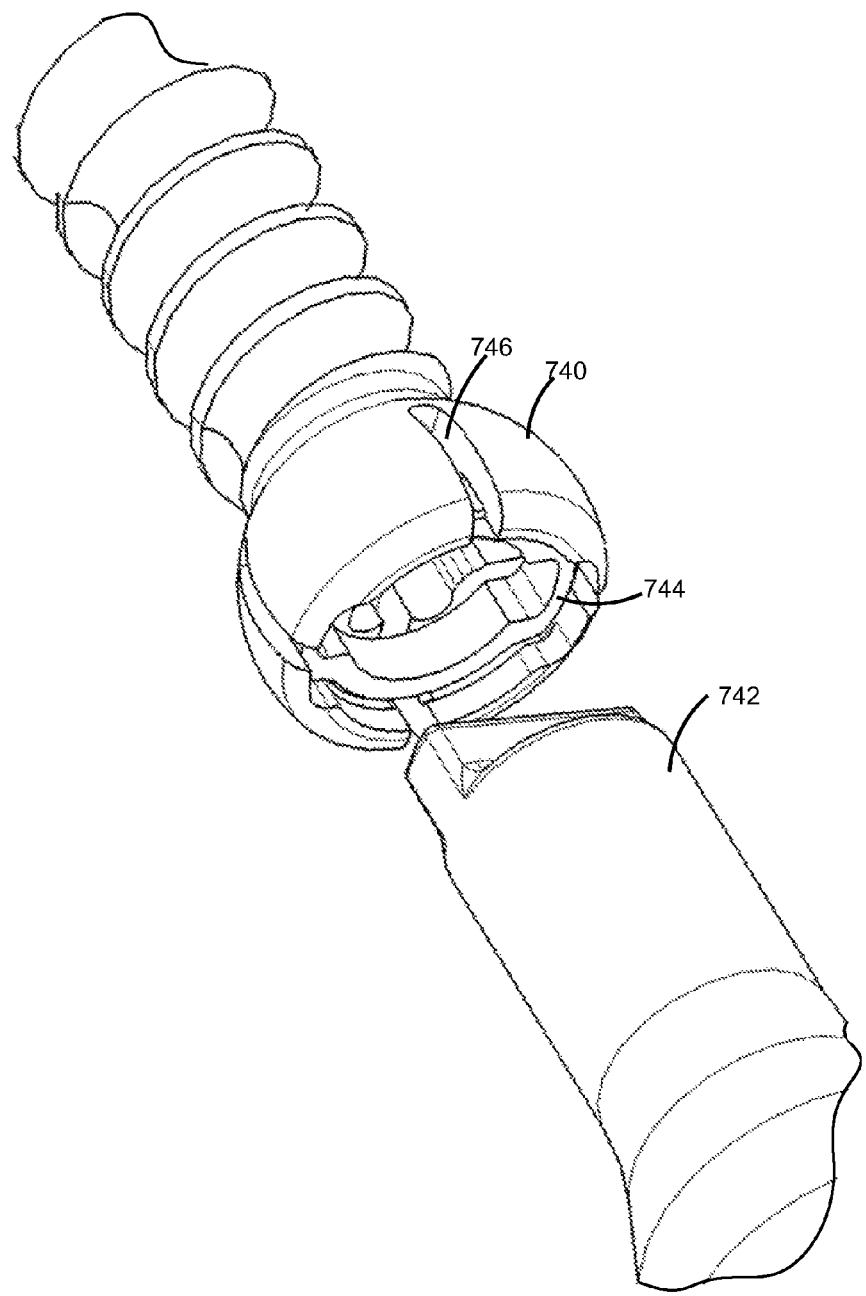
FIG. 29 is a perspective view of a solid expansion tool positioned for insertion into a 4 slot, smooth OD split head fastener in accordance with the invention.
Figure 30:
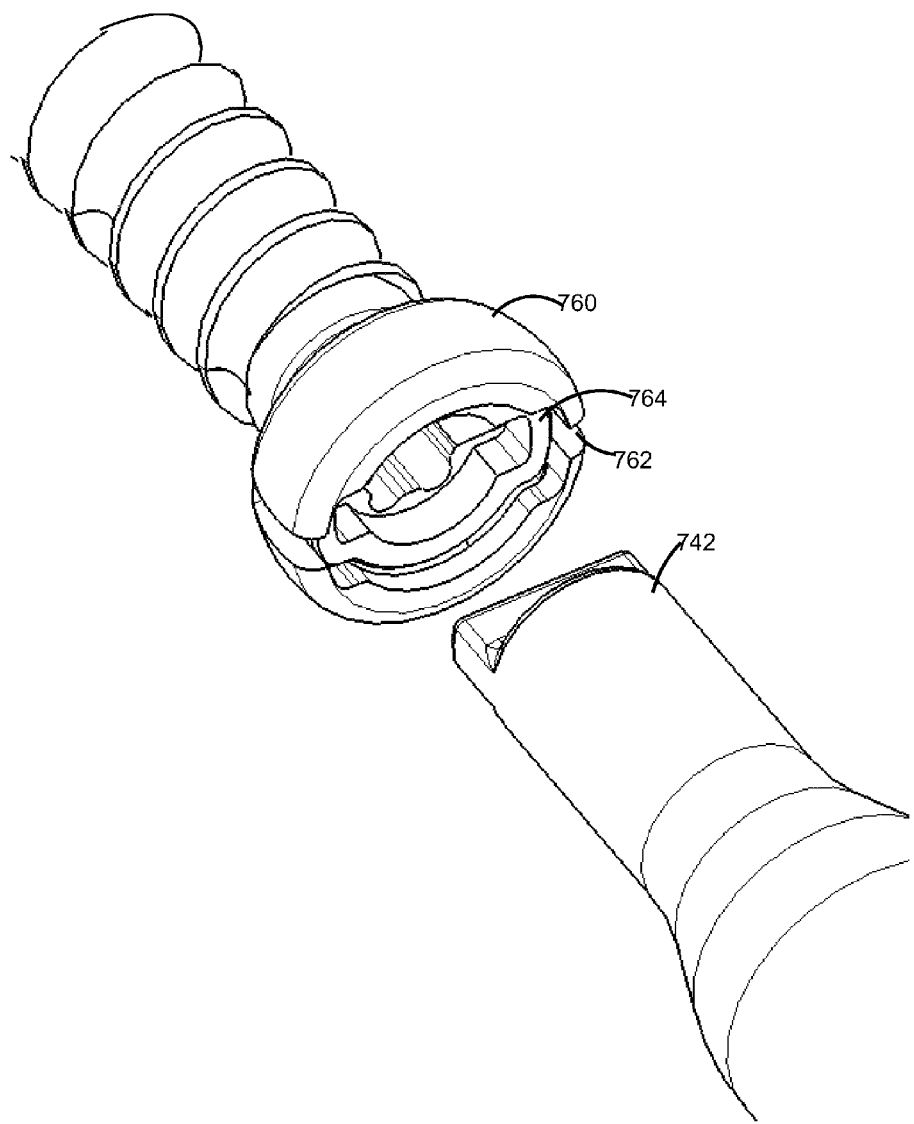
FIG. 30 is a perspective view of a solid expansion tool positioned for insertion into a two slot, smooth OD split head fastener in accordance with the invention.

In FIG. 29 the solid expansion tool 742 is positioned to be inserted into the smooth exterior head 740 having four slots 746. As can be seen the expansion tool 742 aligns with the dual tab locking ring 744. Once inserted the expansion tool 742 rotates the locking ring 744 to apply the appropriate expansion to the head 740 through slots 746. In FIG. 30 the same expansion tool 742 is used with head 760 having two slots 762 and dual tabs 764. As seen, it is preferable that the locking rings having the same number of I tabs have the same dimension, no matter which expansion head being used. This facilitates not only ease of manufacture but convenience of using the same locking tool.

FIG. 31 the interior of the smooth head fastener 802 that positioned to receive the cannulated expansion tool 800. In.

FIGS. 32 and 33 are examples of tools that can be used in conjunction with the disclosed fasteners and are for example only. FIG. 32 is a split lock fastener 822 with a driver bit and expansion tool 820. FIG. 33 illustrates a fastener 832 on a driver 830.

Figure 34:
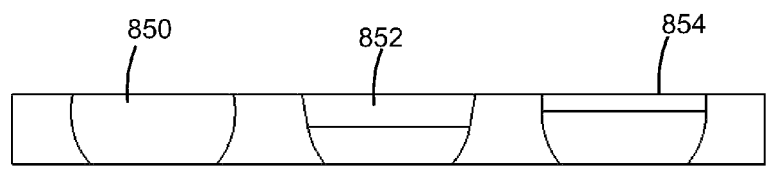
FIG. 34 is a cutaway view of examples of three different receiving holes that can be used in plates to receive the fasteners in accordance with the invention.
Figure 35:
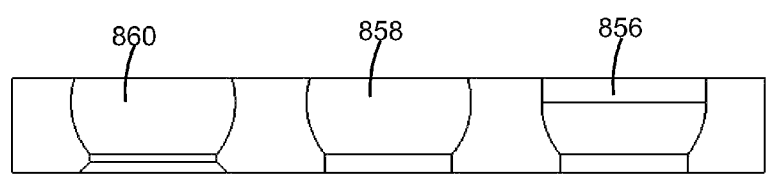
FIG. 35 is a cutaway view of three additional examples of different receiving holes that can be used in plates to receive the fasteners in accordance with the invention.

FIGS. 34 and 35 illustrate examples of plate receiving holes 850, 852, 854, 856, 858, and 860. These are examples only and it should be noted that alternate holes can be used as will be known in the medical arts.

Figure 36:
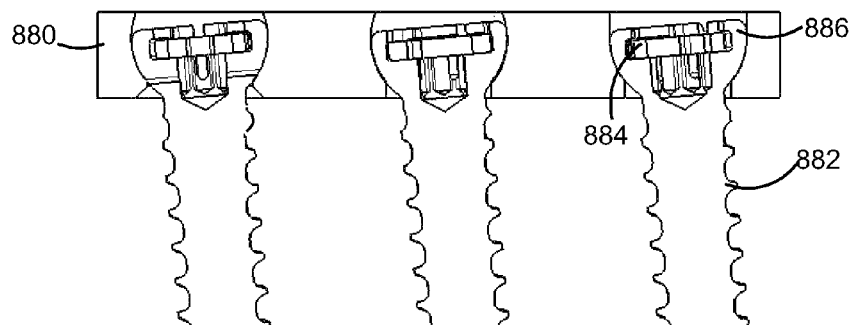
FIG. 36 is a cutaway side view of multiple smooth OD fasteners in a plate in accordance with the invention.
Figure 37:
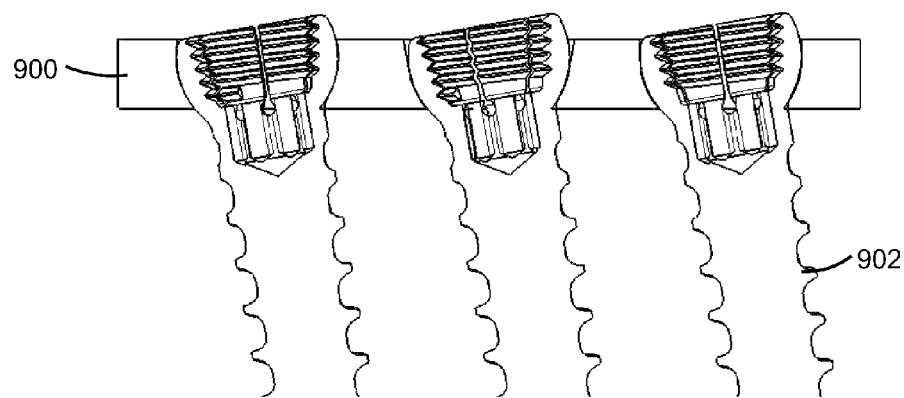
FIG. 37 is a perspective view of fasteners in a multi-fastener plate in accordance with the invention.

FIG. 36 illustrates fasteners 882, inserted into plate 880 at slightly different angles. In FIG. 37 the fasteners 902 are inserted into plate 900 at more of an extreme angle than illustrated in FIG. 36. The fasteners 882, illustrated in FIG. 36 are smooth exterior heads 886 with a locking ring 884 that interacts with the channel, as described heretofore. In FIG. 37, the fasteners 902 have threaded interiors that interact with the threaded locking ring as illustrated in FIGS. 10, 21 and 22.

Figure 38:
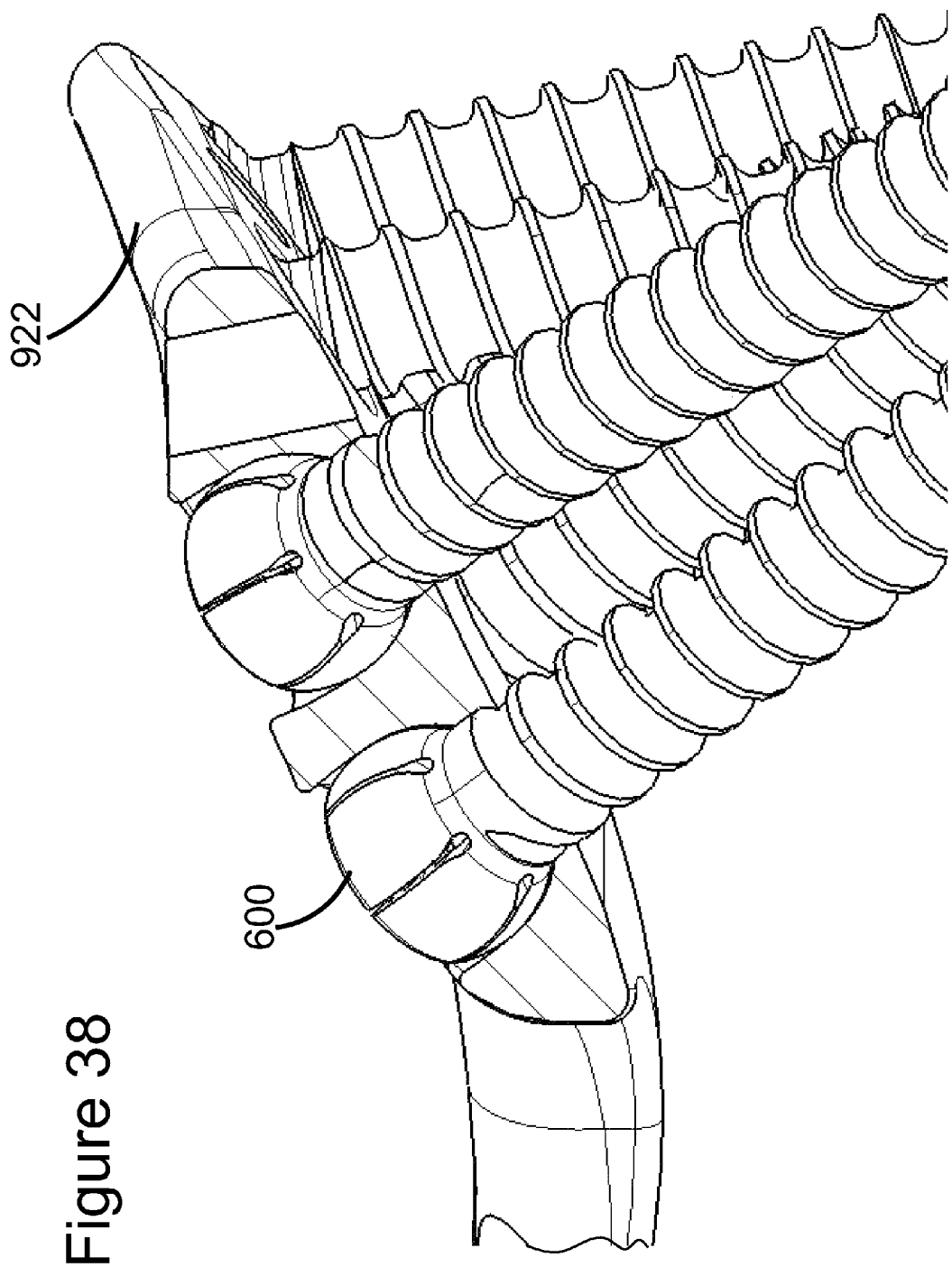
FIG. 38 is a perspective view of fasteners in a multi-fastener plate in accordance with the invention.
Figure 39:
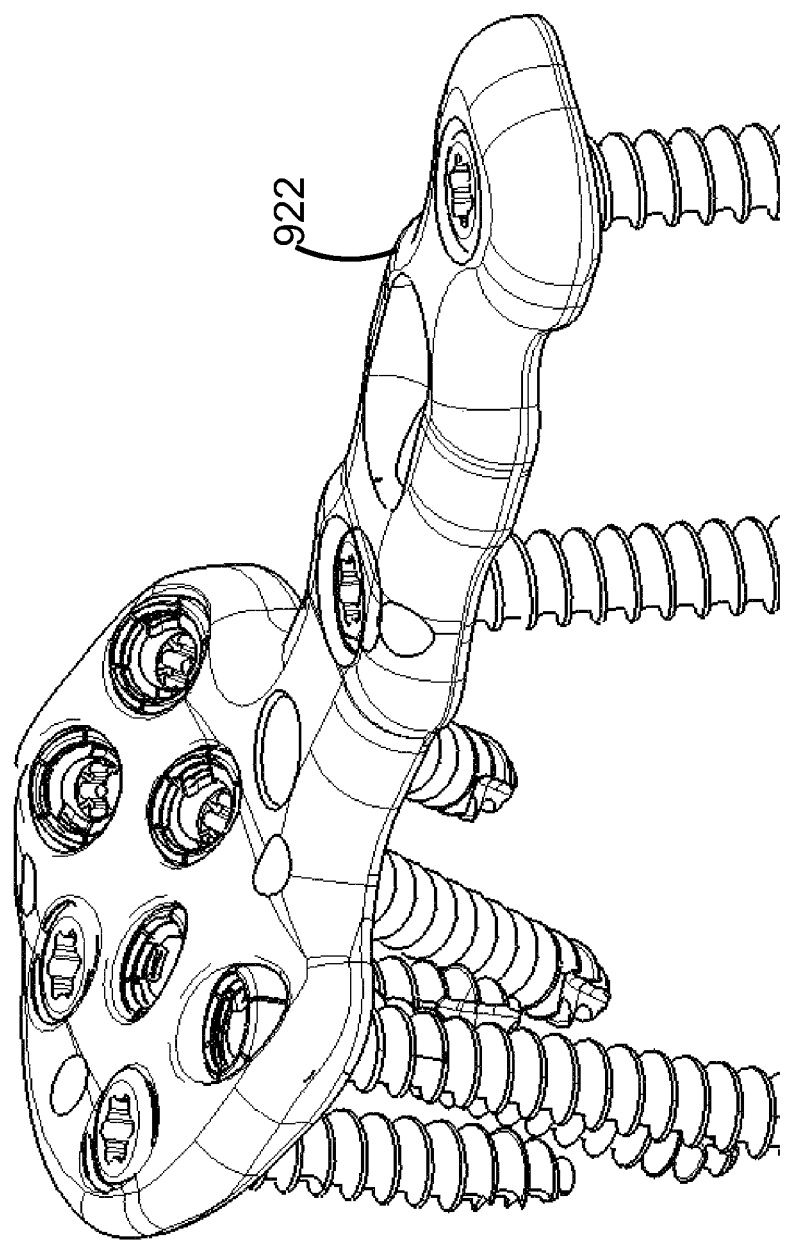
FIG. 39 is a perspective view of fasteners in a multi-fastener plate in accordance with the invention.
Figure 40:
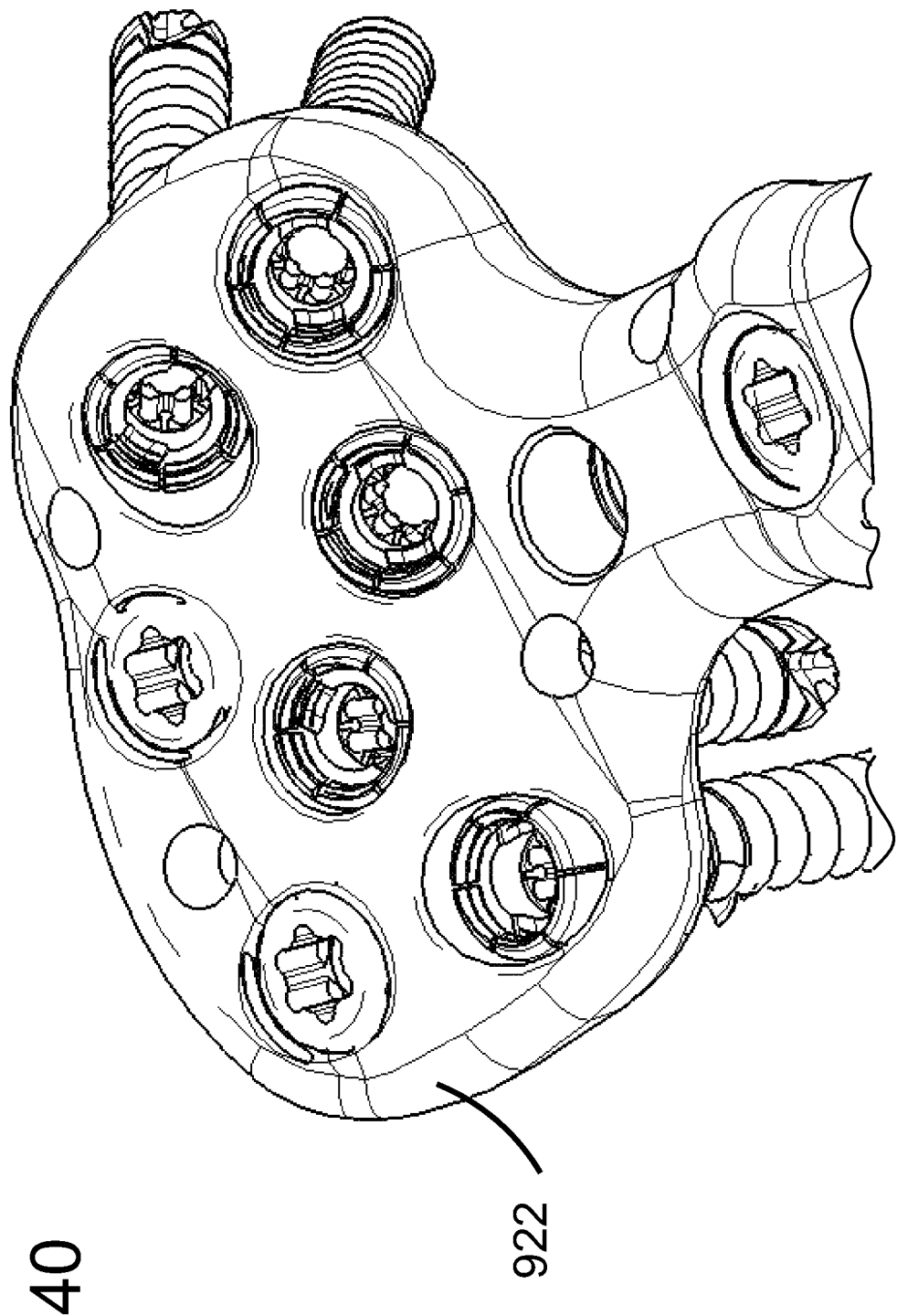
FIG. 40 is a perspective view of fasteners in a multi-fastener plate in accordance with the invention.

In FIG. 38 the smooth outer surface fastener 606 is shown inserted into plate 920 while FIGS. 39 and 40 illustrated fasteners inserted into the plate 922 at various angles to illustrate the versatility of the disclosed system.

Broad Scope of the Invention

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims (e.g., including that to be later added) are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language of the present invention or inventions should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure, the following abbreviated terminology may be employed: "e.g." which means "for example."

What is claimed is:

1. An expansion fastener having a removable locking ring, a head, and a shaft extending from a distal end of said head, said locking ring having an outer periphery, at least one tab, said at least one tab extending beyond said outer periphery and a tool receiving area, said head being substantially cylindrical and having: a proximal end, said proximal end having a first exterior diameter and an open area, said open area having a periphery, an edge, and a base,
   a middle section, said middle section having a tool receiving area contiguous with said open area of said proximal end and a second exterior diameter, said second exterior diameter being greater than said first exterior diameter,
   a distal end, said distal end having a tool receiving area and a third exterior diameter, said third exterior diameter being less than said first exterior diameter and said second exterior diameter,
   a channel along the periphery of said open area between a top rim and said base, said periphery forming a channel wall, said top rim interior diameter being dimensioned to receive said outer periphery of said locking ring,
   at least one tab receiving area within said top rim, each of said at least one tab receiving area being dimensioned to receive said at least one tab, said channel distal said at least one tab receiving area being dimensioned to receive said at least one tab,
   at least one wall periphery reduction along said channel wall adjacent to each of said at least one receiving area and, said periphery reduction being gradual from a minimum reduction end to a maximum reduction end, adjacent to said at least one receiving area, to control expansion adjacent to each of the tab receiving areas,
   at least one slot, said at least one slot extending from said edge of said head toward said distal end, wherein rotation of said locking ring from said receiving area along said wall periphery reduction gradually expands the outer diameter of said head at each of said at least one slot from minimum diameter up to a maximum diameter.

2. The expansion fastener of claim 1 wherein said slot extends from said edge to said base.

3. The expansion fastener of claim 2 further comprising at least one flat, said flat extending from said proximal end to said distal end of said head.

4. The expansion fastener of claim 3 further comprising at least one cutting flute, said cutting flute being adjacent said flat.

5. The expansion fastener of claim 1 further comprising at least one thread on the exterior surface of said head, said thread having a height and a depth and extending from and around said head.

6. The expansion fastener of claim 5 wherein said at least one thread is perpendicular to the axis of said threaded shaft.

7. The expansion fastener of claim 5 wherein said head is spherical and said threads are spherical.

8. The expansion fastener of claim 5 wherein said head is torroidal and said threads are helical.

9. The expansion fastener of claim 1 wherein the exterior of said head is cross-hatched.

10. The expansion fastener of claim 1 wherein said tool receiving area of said locking ring are recesses within a surface of said locking ring.

11. A method of securing biological material to a support material comprising the steps of:
  placing a locking ring having an outer periphery and at least one tab, said at least one tab extending beyond said outer periphery within a receiving area in an expansion fastener having a threaded shaft, a channel along a periphery of an open area between a top rim and a base, said periphery forming a channel wall, said top rim interior diameter being dimensioned to receive said outer periphery of said locking ring, at least one tab receiving area within said top rim, each of said at least one tab receiving area being dimensioned to receive said at least one tab, said channel distal said at least one tab receiving area being dimensioned to receive said at least one tab, and at least one wall periphery reduction along said channel wall adjacent to each of said at least one receiving area;
  aligning said biological material with said support material;
  drilling any required holes in said biological material and said support material;
  threading the fastener through said support material and said biological material;
  rotating said locking ring and gradually expanding said head from an unexpanded position up to a maximum expanded position, to prevent removal of said fastener.

12. The method of claim 11 wherein said biological material is tissue.

13. The method of claim 11 wherein said biological material is bone.

14. The method of claim 11 wherein said support material is a biocompatible plate.

15. The method of claim 11 wherein said support material is bone.

* * * * *